US006905853B1

(12) United States Patent
Wang

(10) Patent No.: US 6,905,853 B1

(45) **Date of Patent: *Jun. 14, 2005**

(54) PHENOL OXIDIZING ENZYME VARIANTS

(75) Inventor: Huaming Wang, Fremont, CA (US)

(73) Assignee: Genencor International, Inc., Palo Alto, CA (US)

(*) Notice: Subject to any disclaimer, the term of this patent is extended or adjusted under 35 U.S.C. 154(b) by 322 days.

This patent is subject to a terminal disclaimer.

(21) Appl. No.: 09/656,640

(22) Filed: Sep. 7, 2000

(51) Int. Cl.[7] ............................ C12N 9/00; C12N 9/02; C07H 21/04

(52) U.S. Cl. ............................... 435/189; 435/4; 435/6; 435/41; 435/183; 435/252.3; 435/254.1; 435/254.11; 435/254.3; 435/254.6; 435/320.1; 435/325; 536/23.2; 536/23.4; 536/23.7; 536/23.74

(58) Field of Search .......................... 435/4, 6, 41, 183, 435/189, 252.3, 254.1, 254.11, 254.3, 254.6, 320.1, 325, 25, 69.1, 440, 471; 536/23.2, 23.4, 23.7, 23.74

(56) References Cited

U.S. PATENT DOCUMENTS 6,168,936 B1 * 1/2001 Wang ......................... 435/189

FOREIGN PATENT DOCUMENTS

| | | |
|---|---|---|
| WO | WO 96/06930 | 3/1996 |
| WO | WO 98/27197 | 6/1998 |
| WO | WO 98/27198 | 6/1998 |
| WO | WO 98/38286 | 9/1998 |
| WO | WO 99/49020 | 9/1999 |
| WO | WO 99/49020 A | 9/1999 |
| WO | WO 00/37654 | 6/2000 |
| WO | WO 01/21809 A | 3/2001 |
| WO | WO 02/20711 A | 3/2002 |

OTHER PUBLICATIONS

Copy of International Search Report for PCT/US 01/27263.
Koikeda, et al., "Molecular Cloning of the Gene for Bilirubin Oxidase from *Myrothecium verrucaria* and Its Expression in Yeast," Journal of Bio. Chem., US, Amer. Soc. of Biolog. Chemists, Baltimore, MD., vol. 268, No. 25, Sep. 5, 1993, pp. 18801–18809 (XP 002139502).
Giardina, P., et al. "The gene, protein and glycan structures of laccase from *Pleurotus ostreatus*" (1996) *Eur. J. Biochem.* vol. 235, pp. 508–515.
Palmieri, G., et al. "Stability and activity of a henol oxidase from the ligninolytic fungus *Pleurotus ostreatus*" (1993) *Appl. Microb. Biotech.* vol. 39, pp. 632–636.
Shimizu, A., et al. "*Myrothecium verrucaria* Bilirubin Oxidase and its Mutants for Potential Copper Ligands" (1999) *Biochem.* vol. 38, pp. 3034–3042.
Xu, F., et al. "Site–directed mutations in fungal laccase: effect on redox potential, activity and pH profile" (1998) *Biochem. J.* vol. 334, pp. 63–70.
Xu, F., et al. "Targeted Mutations in a *Trametes villosa* Laccase" (1999) *J. Biolog. Chem.* vol. 274, No. 18, pp. 12372–12375.

* cited by examiner

*Primary Examiner*—Manjunath N. Rao
(74) *Attorney, Agent, or Firm*—H. Thomas Anderton, Jr.

(57) ABSTRACT

The present invention provides variants of precursor phenol oxidizing enzymes. The precursor enzymes can be, for example, naturally-occurring or recombinant phenol oxidizing enzymes. The variant enzymes, in general, are obtained by modification of a precursor DNA sequence encoding the naturally-occurring or recombinant phenol oxidizing enzyme to generate the substitution of one or more amino acids in the encoded amino acid sequence. Variant enzymes are disclosed having properties which differ from those of their respective precursor enzymes, e.g., altered pH optima and/or phenol oxidizing activity and/or altered stability. The variant enzymes of the present invention are especially useful in detergent formulations, for example, to modify (bleach) the color associated with colored compounds.

19 Claims, 10 Drawing Sheets

```
GGATCCATCA ACATGATCAG CCAAGCTATC GGAGCCGTGG CTCTGGGCCT TGCTGTGATC GGCGGCAGCT CTGTCGATGC 80
CAGATCCGTT GCTGGTCGAT CGACAGACAT GCCTTCCGGT CTCACCAAGA GGCAGACGCA GCTGAGTCCT CCCCTGGCCT 160
TGTACGAAGT GCCTCTGCCG ATCCCTCCTC TGAAGGCGCC CAAGTAGTAA GTACATTCTA TAGGCTAGCA GAGCCAACGT 240
TGCTAATCAT TGCAGTACCG TCCCCAACCC CAACACTGGA GAGGACATCT TGTACTACGA GATGGAGATT AGGCCCTTCT 320
CCCACCAGAT CTACCCTGAT CTGGAGCCGG CCAACATGGT TGGATACGAT GGCATGTCCC CAGGACCTAC CATCATCGTT 400
CCTCGTGGCA CTGAGAGTGT TGTCCGCTTC GTGAACAGCG GAGAGAACAC CTCTCCCAAC AGCGTCCACT TGCACGGCTC 480
TTTCTCTCGA GCTCCCTTTG ATGGTTGGGC TGAGGACACT ACCCAGCCTG GCGAGTACAA GGATTACTAC TACCCCAACA 560
GGCAGGCTGC CCGCATGCTT TGGTACCATG ACCATGCCAT GTCCATCACC GCCGAGAACG CCTACATGGG TCAGGCTGGT 640
GTCTACATGA TCCAGGACCC GGCTGAGGAT GCCCTGAACC TCCCCAGCGG CTACGGCGAG TTTGATATCC CCTTGGTTCT 720
GACTGCCAAG CGATACAACG CAGACGGCAC TCTCTTCTCC ACCAATGGAG AGGTTTCCAG CTTCTGGGGT GACGTTATTC 800
AAGTGGTAAG TTGAGCCCAT TGAGATGCTT CAGATCCTAG AAGTATCGAT GTATGAAATT GTGCATGCTC TAACCAGTGC 880
TATCACAGAA CGGTCAGCCT TGGCCTATGC TCAACGTGCA GCCGCGCAAG TACCCGCTTCC GCTTCCTCAA CGCTGCCGTC 960
TCACGCTCTT TCGCTCTGTA TCTTGCTACC TCTGAGGATT CAGAGACCAG ACTTCCCTTC CAGGTCATTG CCGCTGACGG 1040
TGGTCTGCTT GAGGGCCCTG TTGACACTGA CACTCTGTAC ATCTCTATGG CCGAGCGCTG GGAGGTTGTT ATCGACTTCT 1120
CCACCTTCGC TGGCCAGTCC ATCGATATCC GCAACCTTCC TGGTGCTGAC GGTCTCGGTG TTGAGCCTGA GTTTGATAAC 1200
ACTGACAAGG TCATGCGATT CGTCGTTGAT GAAGTCCTTG AGTCGCCCGA CACTTCTGAG GTGCCTGCCA ACCTCCGAGA 1280
TGTTCCTTTC CCCGAGGGCG GCAACTGGGA CCCCGCAAAC CCCACTGATG ACGAGACTTT CACCTTCGGC CGTGCTAATG 1360
GACAGTGGAC AATCAACGGA GTTACCTTCT CGGATGTCGA GAACCGTCTG CTCCGCAATG TGCCCCGCGA CACTGTTGAG 1440
ATCTGCCGAC TTGAGAACAA CTCCAACGGT TGGACTCACC CTGTTCACAT TCACCTCGTT GACTTCCGAG TCCTTTCTCG 1520
TCCACTGCC CGTGGAGTCG AGCCTTATGA GGCTGCTGGT CTCAAGGATG TTGTCTGGCT GGCTCGTCGT GAGGTTGTCT 1600
ATGTTGAGGC CCACTACGCT CCTTTCCCGT AAGTTCTCGC CTTTTACCTA ACTGGTTTTC ACTCATGCTA ACATCTACAA 1680
GTGGTGTCTA CATGTTGCAC TGCCACAACC TGATCCACGA GGACCACGAC ATGATGGCTG CTTTCAATGT CACTGTTCTC 1760
GGTGACTATG GCTACAACTA CACCGAGTTC ATTGACCCCA TGGAGCCTCT CTGGAGGCCC CGCCCCTTCC TCCTCGGAGA 1840
GTTCGAGAAT GGCTCGGGTG ACTTCAGCGA GCTTGCCATC ACTGACCGCA TTCAGGAGAT GGCTAGCTTC AACCCCTACG 1920
CCCAGGCTGA TGATGATGCC GCTGAGGAGT AGACCGGT. 1958
```

FIGURE 1

```
MISQAIGAVA LGLAVIGGSS VDARSVAGRS TDMPSGLTKR QTQLSPPLAL YEVPLPIPPL 60
KAPNTVPNPN TGEDILYYEM EIRPFSHQIY PDLEPANMVG YDGMSPGPTI IVPRGTESVV 120
RFVNSGENTS PNSVHLHGSF SRAPFDGWAE DTTQPGEYKD YYYPNRQAAR MLWYHDHAMS 180
ITAENAYMGQ AGVYMIQDPA EDALNLPSGY GEFDIPLVLT AKRYNADGTL FSTNGEVSSF 240
WGDVIQVNGQ PWPMLNVQPR KYRFRFLNAA VSRSFALYLA TSEDSETRLP FQVIAADGGL 300
LEGPVDTDTL YISMAERWEV VIDFSTFAGQ SIDIRNLPGA DGLGVEPEFD NTDKVMRFVV 360
DEVLESPDTS EVPANLRDVP FPEGGNWDPA NPTDDETFTF GRANGQWTIN GVTFSDVENR 420
LLRNVPRDTV EIWRLENNSN GWTHPVHIHL VDFRVLSRST ARGVEPYEAA GLKDVVWLAR 480
REVVYVEAHY APFPGVYMLH CHNLIHEDHD MMAAFNVTVL GDYGYNYTEF IDPMEPLWRP 540
RPFLLGEFEN GSGDFSELAI TDRIQEMASF NPYAQADDDA AEE                  583
```

FIGURE 2

```
CAGCTCGGTC TACTACTCTC GCTTCTCTTT GACAAATCAA ATCTACCAAT CGTTCCTTCA ATTTCAAACG ATCAACATGA 80
TCAGCCAAGC TATCGGAGCC GTGGCTCTGG GCCTTGCTGT GATCGGCGGC AGCTCTGTCG ATGCCAGATC CGTTGCTGGT 160
CGATCGACAG ACATGCCTTC CGGTCTCACC AAGAGGCAGA CGCAGCTGAG TCCTCCCCTG GCCTTGTACG AAGTGCCTCT 240
GCCGATCCCT CCTCTGAAGG CGCCCAAGTA GTAAGTACAT TCTATAGGCT AGCAGAGCCA ACGTTGCTAA TCATTGCAGT 320
ACCGTCCCCA ACCCCAACAC TGGAGAGGAC ATCTTGTACT ACGAGATGGA GATTAGGCCC TTCTCCCACC AGATCTACCC 400
TGATCTGGAG CCGGCCAACA TGGTTGGATA CGATGGCATG TCCCCAGGAC CTACCATCAT CGTTCCTCGT GGCACTGAGA 480
GTGTTGTCCG CTTCGTGAAC AGCGGAGAGA ACACCTCTCC CAACAGCGTC CACTTGCACG GCTCTTTCTC TCGAGCTCCC 560
TTTGATGGTT GGGCTGAGGA CACTACCCAG CCTGGCGAGT ACAAGGATTA CTACTACCCC AACAGGCAGG CTGCCCGCAT 640
GCTTTGGTAC CATGACCATG CCATGTCCAT CACCGCCGAG AACGCCTACA TGGGTCAGGC TGGTGTCTAC ATGATCCAGG 720
ACCCGGCTGA GGATGCCCTG AACCTCCCCA GCGGCTACGG CGAGTTTGAT ATCCCCTTGG TTCTGACTGC CAAGCGATAC 800
AACGCAGACG GCACTCTCTT CTCCACCAAT GGAGAGGTTT CCAGCTTCTG GGGTGACGTT ATTCAAGTGG TAAGTTGAGC 880
CCATTGAGAT GCTTCAGATC CTAGAAGTAT CGATGTATGA AATTGTGCAT GCTCTAACCA GTGCTATCAC AGAACGGTCA 960
GCCTTGGCCT ATGCTCAACG TGCAGCCGCG CAAGTACCGC TTCCGCTTCC TCAACGCTGC CGTCTCACGC TCTTTCGCTC 1040
TGTATCTTGC TACCTCTGAG GATTCAGAGA CCAGACTTCC CTTCCAGGTC ATTGCCGCTG ACGGTGGTCT GCTTGAGGGC 1120
CCTGTTGACA CTGACACTCT GTACATCTCT ATGGCCGAGC GCTGGGAGGT TGTTATCGAC TTCTCCACCT TCGCTGGCCA 1200
GTCCATCGAT ATCCGCAACC TTCCTGGTGC TGACGGTCTC GGTGTTGAGC CTGAGTTTGA TAACACTGAC AAGGTCATGC 1280
GATTCGTCGT TGATGAAGTC CTTGAGTCGC CCGACACTTC TGAGGTGCCT GCCAACCTCC GAGATGTTCC TTTCCCCGAG 1360
GGCGGCAACT GGGACCCCGC AAACCCCACT GATGACGAGA CTTTCACCTT CGGCCGTGCT AATGGACAGT GGACAATCAA 1440
CGGAGTTACC TTCTCGGATG TCGAGAACCG TCTGCTCCGC AATGTGCCCC GCGACACTGT TGAGATCTGG CGACTTGAGA 1520
ACAACTCCAA CGGTTGGACT CACCCTGTTC ACATTCACCT CGTTGACTTC CGAGTCCTTT CTCGTTCCAC TGCCCGTGGA 1600
GTCGAGCCTT ATGAGGCTGC TGGTCTCAAG GATGTTGTCT GGCTGGCTCG TCGTGAGGTT GTCTATGTTG AGGCCCACTA 1680
CGCTCCTTTC CCGTAAGTTC TCGCCTTTTA CCTAACTGGT TTTCACTCAT GCTAACATCT ACAAGTGGTG TCTACATGTT 1760
GCACTGCCAC AACCTGATCC ACGAGGACCA CGACATGATG GCTGCTTTCA ATGTCACTGT TCTCGGTGAC TATGGCTACA 1840
ACTACACCGA GTTCATTGAC CCCATGGAGC CTCTCTGGAG GCCCCGCCCC TTCCTCCTCG GAGAGTTCGA GAATGGCTCG 1920
GGTGACTTCA GCGAGCTTGC CATCACTGAC CGCATTCAGG AGATGGCTAG CTTCAACCCC TACGCCCAGG CTGATGATGA 2000
TGCCGCTGAG GAGTAAATAT GATGATCGTC GAATGATTTA TGGACAGCAG TATATAGCTA TTTTAGGAAA TACTTGAATA 2080
AGTTGTGGTG CTTAA 2095
```

FIGURE 3

```
1   MFKHTLGAAALSL.LFNSNAVQASPVP.ETSPATGHLFKRVAQISPQYPM 48
1   MISQAIGAVALGLAVIGGSSVDARSVAGRSTDMPSGLTKRQTQLSPPLAL 50

49  FTVPLPIPPVKQPRLTVTNPVNGQEIWYYEVEIKPFTHQVYPDLGSADLV 98
51  YEVPLPIPPLKAPN.TVPNPNTGEDILYYEMEIRPFSHQIYPDLEPANMV 99

99  GYDGMSPGPTFQVPRGVETVVRFINNAE..APNSVHLHGSFSRAAFDGWA 146
100 GYDGMSPGPTIIVPRGTESVVRFVNSGENTSPNSVHLHGSFSRAPFDGWA 149

147 EDITEPGSFKDYYYPNRQSARTLWYHDHAMHITAENAYRGQAGLYMLTDP 196
150 EDTTQPGEYKDYYYPNRQAARMLWYHDHAMSITAENAYMGQAGVYMIQDP 199

197 AEDALNLPSGYGEFDIPMILTSKQYTANGNLVTTNGELNSFWGDVIHVNG 246
200 AEDALNLPSGYGEFDIPLVLTAKRYNADGTLFSTNGEVSSFWGDVIQVNG 249

247 QPWPFKNVEPRKYRFRFLDAAVSRSFGLYFADTDAIDTRLPFKVIASDSG 296
250 QPWPMLNVQPRKYRFRFLNAAVSRSFALYLATSEDSETRLPFQVIAADGG 299

297 LLEHPADTSLLYISMAERYEVVFDFSDYAGKTIELRNLGGSIGGIGTDTD 346
300 LLEGPVDTDTLYISMAERWEVVIDFSTFAGQSIDIRNLPGA.DGLGVEPE 348

347 YDNTDKVMRFVVADDTTQPDTSVVPANLRDVPFPSPTTNTP......RQF 390
349 FDNTDKVMRFVVDEVLESPDTSEVPANLRDVPFPEGGNWDPANPTDDETF 398

391 RFGRTGPTWTINGVAFADVQNRLLANVPVGTVERWELINAGNGWTHPIHI 440
399 TFGRANGQWTINGVTFSDVENRLLRNVPRDTVEIWRLENNSNGWTHPVHI 448

441 HLVDFKVISRTSGNNARTVMPYE.SGLKDVVWLGRRETVVVEAHYAPFPG 489
449 HLVDFRVLSRST...ARGVEPYEAAGLKDVVWLARREVVYVEAHYAPFPG 495

490 VYMFHCHNLIHEDHDMMAAFNATVLPDYGYNATVFVDPMEELWQARPYEL 539
496 VYMLHCHNLIHEDHDMMAAFNVTVLGDYGYNYTEFIDPMEPLWRPRPFLL 545

540 GEFQAQSGQFSVQAVTERIQTMAEYRPYAAADE 572
546 GEFENGSGDFSELAITDRIQEMASFNPYAQADD 578
```

FIGURE 4

PHENOL OXIDIZING ENZYME VARIANTS

FIELD OF THE INVENTION

The present invention relates to phenol oxidizing enzymes. More particularly, the invention relates to phenol oxidizing enzymes that have been modified so as to exhibit one or more altered properties, such as pH optimum, phenol oxidizing activity, stability, substrate specificity, etc. The present invention further provides methods and host cells for expressing variant phenol oxidizing enzymes as well as methods for producing expression systems.

BACKGROUND OF THE INVENTION

Phenol oxidizing enzymes function by catalyzing redox reactions, i.e., the transfer of electrons from an electron donor (usually a phenolic compound) to molecular oxygen (which acts as an electron acceptor) which is reduced to $H_2O$. While being capable of using a wide variety of different phenolic compounds as electron donors, phenol oxidizing enzymes are very specific for molecular oxygen as the electron acceptor.

Phenol oxidizing enzymes can be utilized for a wide variety of applications in a number of industries, including the detergent industry, the paper and pulp industry, the textile industry and the food industry. In one application, phenol oxidizing enzymes are used as an aid in the removal of stains, such as food stains, from clothes during detergent washing.

Most phenol oxidizing enzymes exhibit pH optima in the acidic pH range while being inactive in neutral or alkaline pHs.

Phenol oxidizing enzymes are known to be produced by a wide variety of fungi, including species of the genii *Aspergillus, Neurospora, Podospora, Botrytis, Pleurotus, Fornes, Phlebia, Tranmetes, Polyporus, Rhizoctonia, Bipolaris, Curvularia, Amerosporium,* and *Lentinus.* However, there remains a need for phenol oxidizing enzymes having pH optima in the alkaline range for use in detergent washing methods and compositions.

SUMMARY OF THE INVENTION

The present invention relates to phenol oxidizing enzymes, and especially to mutants or variants of "precursor phenol oxidizing enzymes". In a preferred embodiment, the present invention relates to variants of a precursor phenol oxidizing enzyme obtainable from *Stachybotrys.* In particular, the enzyme variants of the present invention are capable of modifying the color associated with colored compounds having different chemical structures, especially at neutral or alkaline pH. Based on their color modifying ability, phenol oxidizing enzyme variants of the present invention can be used, for example, for pulp and paper bleaching, for bleaching the color of stains on fabric and in detergent and textile applications. In one aspect of the present invention, the phenol oxidizing enzyme variant is able to modify the color of a colored compound in the absence of an enhancer. In another aspect of the present invention, the phenol oxidizing enzyme variant is able to modify the color in the presence of an enhancer.

One embodiment of the present invention is based upon the identification and characterization of a genomic sequence (SEQ ID NO:3) encoding a phenol oxidizing enzyme obtainable from *Stachybotrys* and having the deduced amino acid sequence as shown in SEQ ID NO:2.

These sequences provide, respectively, a preferred "precursor nucleic acid sequence" and a corresponding encoded "precursor phenol oxidizing enzyme" which are useful in preparing the phenol oxidizing enzyme variants herein.

In an exemplary embodiment, the present invention provides precursor phenol oxidizing enzymes having amino acid sequences comprising from at least about 68% to about 100% identity (that is, at least 68%, at least 70%, at least 75%, at least 80%, at least 85%, at least 90%, at least 95%, and 100%) identity to the amino acid sequence disclosed in SEQ ID NO:2, as long as the enzyme is capable of modifying the color associated with colored compounds. In one embodiment, the precursor phenol oxidizing enzyme has the amino acid sequence as shown in SEQ ID NO:2 or as contained in *Stachybotrys chartarum* having MUCL accession number 38898.

In one embodiment, the precursor phenol oxidizing enzyme is obtainable from a *Stachybotrys* species including *Stachybotrys parvispora, Stachybotrys chartarum; S. kampalensis; S. theobromae; S. bisbyi, S. cylindrospora, S. dichroa, S. oenanthes* and *S. nilagerica.* In another embodiment, the *Stachybotrys* includes *Stachybotrys chartarum* MUCL 38898 and *S. chartarum* MUCL 30782.

In yet another embodiment, the present invention encompasses an isolated polynucleotide encoding a preferred precursor phenol oxidizing enzyme, the nucleic acid sequence itself thus being a "precursor nucleic acid sequence" for use herein, wherein said polynucleotide comprises a nucleic acid sequence having between at least about 65% and 100% identity (that is, at least 65%, at least 70%, at least 75%, at least 80%, at least 85%, at least 90%, and at least 95%) identity to SEQ ID NO:1, as long as the polynucleotide encodes a phenol oxidizing enzyme capable of modifying the color associated with colored compounds. In certain embodiments, preferred precursor nucleic acid sequences for use herein are able to hybridize under conditions of intermediate to high stringency to the polynucleotide shown in SEQ ID NO:1 or SEQ ID NO:3, as long as the encoded protein is capable of modifying the color associated with colored compounds. The present invention also encompasses precursor polynucleotides that encode the amino acid sequence as shown in SEQ ID NO:2. In one embodiment, the polynucleotide has the nucleic acid sequence as shown in SEQ ID NO:1 or SEQ ID NO:3 or as contained in *Stachybotrys chartarum* having MUCL accession number 38898. The present invention also provides expression vectors and host cells comprising precursor nucleic acid sequences of the present invention.

The present invention additionally relates to methods for producing precursor phenol oxidizing enzymes as well as phenol oxidizing enzyme variants of the present invention. Accordingly, the present invention provides a method for producing a phenol oxidizing enzyme comprising the step of culturing a host cell comprising an isolated polynucleotide encoding a selected phenol oxidizing enzyme under conditions suitable for the production of the phenol oxidizing enzyme; and optionally recovering the phenol oxidizing enzyme produced. In one embodiment, the polynucleotide comprises the sequence as shown in SEQ ID NO:1 or a mutant thereof. In another embodiment, the polynucleotide comprises the sequence as shown in SEQ ID NO:3 or a mutant thereof. In an additional embodiment, the polynucleotide hybridizes under conditions of intermediate to high stringency with the polynucleotide having the sequence as shown in SEQ ID NO:1 or SEQ ID NO:3 or as contained in *Stachybotrys chartarum* having MUCL accession number 38898. In a further embodiment, the polynucleotide has between 65% and 100% identity, that is, at least 65%, at least 70%, at least 75%, at least 80%, at least 85%, at least 90% and at least 95% identity, to SEQ ID NO: 1 or SEQ ID NO:3.

The present invention also provides a method for producing a recombinant host cell comprising a polynucleotide encoding a precursor phenol oxidizing enzyme or a phenol oxidizing enzyme variant, comprising the steps of obtaining an isolated polynucleotide encoding said precursor or variant; introducing said polynucleotide into said host cell; and growing said host cell under conditions suitable for the production of said precursor or variant. In one embodiment, the polynucleotide is integrated into the host genome; and in another embodiment, the polynucleotide is present on a replicating plasmid.

The host cell comprising a polynucleotide encoding a precursor or variant enzyme can be, for example, a filamentous fungus, yeast or bacteria. In one embodiment, the host cell is a filamentous fungus, such as *Aspergillus* species, *Trichoderma* species and *Mucor* species. In another embodiment, the filamentous fungus host cell is *Aspergillus niger* var. *awamori* or *Trichoderma reseei.* In another embodiment of the present invention, the host cell is a yeast which includes *Saccharomyces, Pichia, Hansenula, Schizosaccharomyces, Kluyveromyces* and *Yarrowia* species. In yet another embodiment, the *Saccharomyces* species is *Saccharomyces cerevisiae.* In an additional embodiment, the host cell is a bacteria including gram positive bacteria, such as a *Bacillus* species, and gram negative bacteria, such as an *Escherichia* species.

Also provided herein are enzymatic compositions comprising an amino acid sequence having between at least about 68% and less than 100% identity to the amino acid sequence of *Stachybotrys* oxidase B enzyme (SEQ ID NO:2). That is, the amino acid sequence has at least 68% and less than 100%, at least 70% and less than 100%, at least 75% and less than 100%, at least 80% and less than 100%, at least 85% and less than 100%, at least 90% and less than 100%, and/or at least 95% and less than 100% identity to the amino acid sequence of SEQ ID NO:2. In one embodiment, the amino acid sequence is like the sequence as shown in SEQ ID NO:2 except that it differs from said SEQ ID NO:2 sequence in at least one of the positions 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573, or sequence positions corresponding thereto. Such enzymatic compositions can be used, for example, in the fields of bleaching, cleaning, personal care, food, feed, pulp and paper, textile, leather, contact lens cleaning, and starch. The enzymatic compositions of the invention can be used, for example, for producing detergents and other cleaning compositions; compositions for use in pulp and paper applications; and textile applications.

The present invention also encompasses methods for modifying the color associated with colored compounds which occur in stains on samples, comprising the steps of contacting the sample with a composition comprising an amino acid sequence having between at least 68% and less than 100% identity to the amino acid sequence of *Stachybotrys* oxidase B enzyme (SEQ ID NO:2), as long as the enzyme is capable of modifying the color associated with colored compounds. In a preferred embodiment of the method, the amino acid is like the sequence as shown in SEQ ID NO:2 except that it differs from said SEQ ID NO:2 sequence in at least one of the positions 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573, or sequence positions corresponding thereto.

In one aspect of the invention, the pH optimum for a phenol oxidizing enzyme variant of the present invention is between 5.0 and 11.0, in another aspect, the pH optimum is between 7 and 10.5 and in yet another aspect the pH optimum is between 8.0 and 10. In a further aspect of the invention, the optimum temperature is between 20 and 60 degrees C., and in another aspect between 20 and 40 degrees C.

BRIEF DESCRIPTION OF THE DRAWINGS

FIG. 1 provides the nucleic acid sequence (SEQ ID NO:1) for a phenol oxidizing enzyme obtainable from *Stachybotrys chartarum* by PCR as described in Example 5.

FIG. 2 provides the amino acid sequence (SEQ ID NO:2) for the protein designated herein as the *Stachybotrys* phenol oxidase B enzyme.

FIG. 3 illustrates the genomic sequence (SEQ ID NO:3) for a phenol oxidizing enzyme obtainable from *Stachybotrys chartarum.* This nucleic acid sequence is referred to herein as *Stachybotrys* phenol oxidase B gene.

FIG. 4 is an amino acid alignment of *Stachybotrys* phenol oxidase B enzyme SEQ ID NO:2 (bottom line) and Bilirubin oxidase (SEQ ID NO:4).

DETAILED DESCRIPTION

Figure 5:
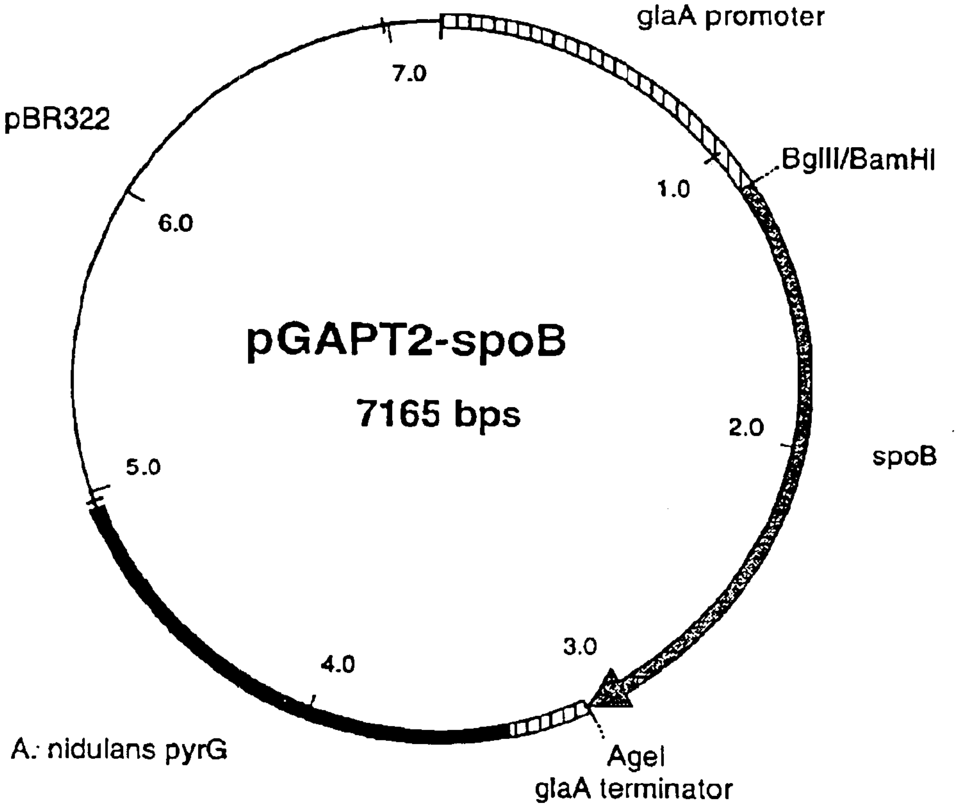
FIG. 5 provides an illustration of the vector pGAPT2-spoB which was used for the expression of *Stachybotrys* phenol oxidizing enzyme in *Aspergillus.* Base 1 to 1134 contains *Aspergillus niger* glucoamylase gene promoter. Base 3098 to 3356 and 4950 to 4971 contains *Aspergillus niger* glucoamylase terminator. *Aspergillus nidulans* pyrG gene was inserted from 3357 to 4949 as a marker for fungal transformation. The rest of the plasmid contains pBR322 sequences for propagation in *E. coli.* Nucleic acid encoding the *Stachybotrys* phenol oxidizing enzyme of SEQ ID NO:1 was cloned into the Bgl II and Age I restriction sites.

The inventors have discovered that various single and multiple mutations involving the substitution, deletion and/or insertion of one or more amino acids within a precursor phenol oxidizing enzyme amino acid sequence can confer advantageous properties to such mutants or variants when compared to the precursor enzyme.

In one embodiment, *Stachybotrys* phenol oxidase B enzyme, a phenol oxidizing enzyme, is isolated and then mutated by modifying the DNA encoding the enzyme to encode the substitution of one or more amino acids at various amino and residues within the mature form of the molecule. In further embodiments, enzymatically active variants of *Stachybotrys* phenol oxidase B enzyme, acting in turn as further precursor enzymes, are modified in a similar fashion to provide still further variants. Preferred variants have at least one property which is different when compared to the same property of a precursor enzyme. These modified properties fall into several categories including: hyperproduction suitability, oxidative stability, substrate specificity, thermal stability, alkaline stability, catalytic activity, pH activity profile, resistance to proteolytic degradation.

Definitions

In order to describe enzyme variants according to the invention, the following nomenclature is used: original amino acid; position from N-terminus of the enzyme; substituted amino acid. For example, the substitution of methionine with phenylalanine at position 254 in the amino acid sequence of Seq ID No:2 is shown as M254F. Individual substitutions of multiple substitutions or substitution sets are shown separated by a forward slash (/); e.g. M254F/S272L.

As used herein, the term "phenol oxidizing enzyme" refers to those enzymes, both naturally-occurring and recombinant, which are capable of catalyzing redox reactions wherein the electron donor is a phenolic compound and which are specific for molecular oxygen or hydrogen peroxide as the electron acceptor.

A "recombinant" phenol oxidizing enzyme is one in which the nucleic acid sequence encoding the enzyme is modified to produce a variant or mutant nucleic acid sequence which encodes the substitution, deletion or insertion of one or more amino acids in the naturally-occurring amino acid sequence. Suitable methods to produce such modification, and which may be combined with those disclosed herein, include those disclosed in U.S. Pat. RE 34,606, U.S. Pat. No. 5,204,015 and U.S. Pat. No. 5,185,258, U.S. Pat. No. 5,700,676, U.S. Pat. No. 5,801,038, and U.S. Pat. No. 5,763,257.

As used herein, the terms "mutants" and "variants", when referring to phenol oxidizing enzymes, refer to phenol oxidizing enzymes obtained by alteration of a precursor amino acid sequence and/or structure thereof, such as by alteration of the nucleotide sequence of the structural gene and/or by direct substitution and/or alteration of the amino acid sequence and/or structure of the phenol oxidizing enzyme. Such terms are also understood to include naturally occurring variants. Further included are portions or fragments of full-length precursor enzymes, naturally occurring or recombinant, that retain at least one activity of the precursor phenol oxidizing enzyme. As used herein, the terms "mutants" and "variants", when referring to microbial strains, refer to cells that are changed from a natural isolate in some form, for example, having altered DNA nucleotide sequence of, for example, the structural gene coding for a phenol oxidizing enzyme variant; alterations to a natural isolate in order to enhance phenol oxidizing enzyme production; or other changes that effect phenol oxidizing enzyme expression.

The phenol oxidizing enzyme variants of the present invention include the mature forms of enzyme variants, as well as the pro- and prepro-forms of such variants.

A phenol oxidizing enzyme variant has an amino acid sequence which is derived from the amino acid sequence of a "precursor phenol oxidizing enzyme". Suitable precursor enzymes include naturally-occurring enzymes and recombinant enzymes. The amino acid sequence of the variant is "derived" from the precursor amino acid sequence by the substitution, deletion or insertion of one or more amino acids of the precursor amino acid sequence. Typically, such modification is of the "precursor nucleic acid sequence" which encodes the amino acid sequence of the precursor phenol oxidizing enzyme. In such case, the nucleic acid sequence encoding the variant is "derived" from the precursor nucleic acid sequence. Suitable methods for such manipulation of the precursor nucleic acid sequence include methods disclosed herein, as well as methods known to those skilled in the art (see, for example, EP 0 328299, WO 89/06279).

It should be appreciated that suitable precursor enzymes useful herein include wild type phenol oxidizing enzymes as well as mutant or variant enzymes. Thus, in some instances, a phenol oxidizing enzyme variant of the present invention may have a lineage that includes more than one precursor enzyme; e.g., a variant of the invention could be derived from a variant enzyme which in turn was derived from a wild type enzyme. The wild type enzyme, in such a case, is a precursor enzyme, as is the intervening variant.

As used herein, *Stachybotrys* refers to any *Stachybotrys* species which produces a phenol oxidizing enzyme capable of modifying the color associated with colored compounds. The present invention encompasses derivatives of natural isolates of *Stachybotrys,* including progeny, mutants or variants, as long as the derivative is able to produce a phenol oxidizing enzyme capable of modifying the color associated with colored compounds.

As used herein in referring to phenol oxidizing enzymes, the term "obtainable from" means phenol oxidizing enzymes that originate from or are naturally-produced by the particular microbial strain mentioned. To exemplify, phenol oxidizing enzymes obtainable from *Stachybotrys* refer to those phenol oxidizing enzymes which are naturally-produced by *Stachybotrys.* Also included are phenol oxidizing enzymes identical to those produced by *Stachybotrys* species but which are produced through the use of genetic engineering techniques by organisms, such as bacteria, fungus or yeast, transformed with a gene encoding said phenol oxidizing enzyme or produced by organisms which are identical to those from *Stachybotrys,* or equivalent to those from *Stachybotrys,* such as progeny or mutants.

As used herein, the term 'colored compound' refers to a substance that adds color to textiles or to substances which result in the visual appearance of stains. As defined in Dictionary of Fiber and Textile Technology (Hoechst Celanese Corporation (1990) PO Box 32414, Charlotte, N.C. 28232), a dye is a colored compound that is incorporated into the fiber by chemical reaction, absorption, or dispersion. Examples include direct Blue dyes, acid Blue dyes, direct red dyes, reactive Blue and reactive Black dyes. A catalogue of commonly used textile dyes is found in Colour Index, $3^{rd}$ ed. Vol. 1–8. Examples of substances which result in the visual appearance of stains are polyphenols, carotenoids, anthocyanins, tannins, Maillard reaction products, etc.

As used herein the phrase "modify the color associated with a colored compound" or "modification of the colored compound" means that the colored compound is changed through oxidation, either directly or indirectly, such that either the color appears modified, i.e., the color visually appears to be decreased, lessened, decolored, bleached or removed. The present invention encompasses the modification of the color by any means including, for example, the complete removal of the colored compound from stain on a fabric by any means as well as a reduction of the color intensity or a change in the color of the compound.

The term "enhancer" or "mediator" refers to any compound that is able to modify the color associated with a colored compound in association with a phenol oxidizing enzyme or a compound which increases the oxidative activity of the phenol oxidizing enzyme. The enhancing agent is typically an organic compound.

Phenol Oxidizing Enzyme Variants

The phenol oxidizing enzyme variants of the present invention function by catalyzing redox reactions, i.e., the transfer of electrons from an electron donor (usually a phenolic compound) to molecular oxygen or hydrogen peroxide (which acts as an electron acceptor) which is reduced to water. The variants can be, for example, enzymatically active, mutated laccases (EC 1.10.3.2), mutated bilirubin oxidases (EC 1.3.3.5), mutated phenol oxidases (EC 1.14.18.1), mutated catechol oxidases (EC 1.10.3.1).

An exemplary phenol oxidizing enzyme of the present invention is a variant or mutant of a precursor enzyme, which precursor enzyme has from 68% to 100% identity to the amino acid sequence of *Stachybotrys* phenol oxidase B enzyme (shown in SEQ ID NO:2). That is, the amino acid sequence of the precursor enzyme is at least 68%, at least 70%, at least 75%, at least 80%, at least 85%, at least 90%, at least 95%, or 100% identical to the amino acid sequence of *Stachybotrys* phenol oxidase B enzyme (SEQ ID NO:2). The present invention encompasses phenol oxidizing enzyme variants of such a precursor enzyme, wherein the variant comprises a sequence that differs from that of the precursor in at least one of the positions 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573, or sequence positions corresponding thereto. Typical variant enzymes, in accordance with the teachings herein, will have at least 68% and less than 100% identity to the amino acid sequence of *Stachybotrys* phenol oxidase B enzyme (SEQ ID NO:2). That is, the amino acid sequence of such variants will have at least 68% and less than 100%, at least 70% and less than 100%, at least 75% and less than 100%, at least 80% and less than 100%, at least 85% and less than 100%, at least 90% and less than 100%, or at least 95% and less than 100% identity to the amino acid sequence of *Stachybotrys* oxidase B enzyme (SEQ ID NO:2). As used herein, identity is measured by the GAP program of GCG software (University Research Park, Madison, Wis.) with the following parameters: Gap Weight=12; Length Weight=4; Gap Creation Penalty=8; and Gap Extension Penalty=2.

Specific residues corresponding to positions 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573, of *Stachybotrys* oxidase B enzyme are identified herein for substitution, insertion or deletion. These amino acid position numbers refer to those assigned to the *Stachybotrys* oxidase B enzyme sequence as presented in SEQ ID NO:2. The invention, however, is not limited to the mutation of this particular oxidase enzyme but extends to precursor phenol oxidizing enzymes containing amino acid residues at positions which are "equivalent" to the particular identified residues in *Stachybotrys* phenol oxidase B enzyme.

A residue (amino acid) of a precursor phenol oxidizing enzyme is equivalent to a residue of *Stachybotrys* oxidase B enzyme it if is either homologous (i.e., corresponding in position in either primary or tertiary structure) or analogous to a specific residue or portion of that residue in *Stachybotrys* oxidase B enzyme (i.e., having the same or similar functional capacity to combine, react, or interact chemically).

In one preferred embodiment, a variant enzyme of the present invention has a sequence that differs from that of *Stachybotrys* phenol oxidase B enzyme (SEQ ID NO:2) in at least one of the positions 188, 254, 272, 346, 348, 394, and 425. One such variant includes an amino acid substitution in position 254 (e.g., M254 substituted with one of the following: F, N, L, K, A, I, E, S, H, V, T, P, G, or C) and an additional substitution in at least one of the positions 48, 67, 70, 76, 83, 98, 115, 119, 134, 171, 175, 177, 179, 188, 236, 246, 253, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573; with preferable additionally substituted positions being 76, 188, 272, 302, 346, 348, 394, and 425 (e.g., a 76/254/302/188 variant; a 76/254/302 variant; a 254/394 variant; a 254/346/348 variant; or a 254/272 variant). Another such variant includes the substitution set 394/425 (e.g. D394N/V425M); and optionally further includes a substitution in at least one of the positions 76, 254, and 302 (e.g., a 254/76/302/394/425 variant). Still a further preferred variant of the present invention has a sequence that differs from that of *Stachybotrys* phenol oxidase B enzyme (SEQ ID NO:2) only at position 254 ( e.g., at M254F variant).

Certain preferred multiply-substituted variants (i.e., variants having substitution sets) of the present invention include (corresponding to positions of *Stachybotrys* phenol oxidase B enzyme (SEQ ID NO:2)):

| |
|---|
| 48/254 |
| 67/254 |
| 70/119/254 |
| 70/254 |
| 76/188/254/302 |
| 76/254 |
| 76/254/302 |
| 76/254/302/394/425 |
| 83/254 |
| 98/254 |
| 119/254/269 |
| 119/254/329 |
| 119/254/346 |
| 119/254/390 |
| 119/254/415 |
| 134/177 |
| 171/172/254/346/348 |
| 171/254/346 |
| 171/254/346/348 |
| 179/254 |
| 180/181/254 |
| 181/254 |
| 188/236/254/272/346/348/394 |
| 188/236/254/346/348/394 |
| 188/254 |
| 236/254 |
| 246/254 |
| 254/269 |
| 254/272 |
| 254/296 |
| 254/302/346 |
| 254/302/346/348 |
| 254/308 |
| 254/318 |
| 254/329 |
| 254/331 |
| 254/346 |

-continued

| |
|---|
| 254/346/348 |
| 254/349 |
| 254/365 |
| 254/390 |
| 254/394 |
| 254/394/425 |
| 254/404 |
| 254/415 |
| 254/423 |
| 254/428 |
| 254/434 |
| 254/465 |
| 254/479 |
| 254/481 |
| 254/483 |
| 254/499 |
| 254/550 |
| 254/573 |
| 254/573/570 |
| 394/425 |

Certain particularly preferred phenol oxidizing enzyme variants include an amino acid substitution at one or more of the positions or position sets (corresponding to positions of *Stachybotrys* phenol oxidase B enzyme (SEQ ID NO:2)): 76/254/302; 76/254/302/188; 76/254/302/394/425; 119/254/329; 119/254/390; 119/254/415; 171/254/346; 236/254; 254; 254/272; 254/302/346/348; 254/346/348; 254/394; 254/550; and/or 394/425.

Particular substitutions and substitution sets of the present invention, relative to the amino acid sequence of *Stachybotrys* phenol oxidase B enzyme (SEQ ID NO:2), include:

| |
|---|
| N391S |
| G115S |
| D562G |
| D394N/V425M |
| V134I/H177Y |
| L499F |
| M254F |
| M254F/L499F |
| M98L/M254F |
| L76W/M254F |
| M254F/F349Y |
| H175V |
| H177V |
| L76W/M254F/E302V |
| M254F/D394N/V425M |
| L76W/M254F/E302V/D394N/V425M |
| M254F/W318Y |
| M254F/L48Y |
| M254F/R83K |
| M254F/M188F |
| M254F/Q246H |
| M254F/S331T |
| M254F/V483T |
| M254F/R67T |
| V119L/M254F/N70V |
| M254F/N70V |
| M254F/D308S |
| M254F/E365T |
| M254F/S415A |
| M254F/R423A |
| M254F/D428G |
| M254F/R434E |
| M254F/E465M |
| M254F/A479G |
| M254F/N550A |
| P253A |
| V119L/M254F/A269M |
| M254F/A269M |
| V119L/M254F/G329N |
| M254F/G329N |

-continued

| |
|---|
| M254F/S331A |
| M254F/E346V/E348Q |
| V119L/M254F/E346V |
| M254F/E346V |
| V119L/M254F/A390P |
| M254F/A390P |
| M254F/N404T |
| V119L/M254F/S415L |
| M254F/S415L |
| M254F/R481G |
| M254F/A573N |
| M254F/A573N/F570L |
| M254F/L76W/E302V/M188K |
| M254N |
| M254L |
| M254A |
| M254I |
| M254E |
| M254S |
| M254H |
| M254V |
| M254T |
| M254P |
| W254G |
| M254K |
| M254C |
| M254F/D394G |
| M254F/D394V |
| M254F/D394S |
| M254F/D394H |
| M254F/D394P |
| M254F/D394Y |
| M254F/D394W |
| M254F/D394N |
| M254F/M179F |
| M254F/M179V |
| M254F/M179P |
| M254F/M179G |
| M254F/M179E |
| M254F/M179L |
| M254F/I181D |
| M254F/S180F/I181L |
| M254F/E346V/E302I |
| M254F/E346V/E302K |
| M254F/E346V/E348Q/E302F |
| M254F/E346V/E348Q/E302A |
| M254F/E346V/E348Q/E302L |
| M254F/E346V/E302C |
| M254F/E346V/E302V |
| M254F/E346V/M171T |
| M254F/E346V/E348Q(M171P |
| M254F/E346V/E348Q/M171L |
| M254F/E346V/M171Y |
| M254F/E346V/E348Q/M171V |
| M254F/E346V/M171S |
| M254F/E346V/M171R |
| M254F/E346V/E348Q/M171F |
| M254F/E346V/M171K |
| M254F/E346V/E348Q/M171Q |
| M254F/E346V/E348Q/M171N |
| M254F/E346V/E348Q/M171N/L172H |
| M254F/S272L |
| M254F/E236K |
| M254F/E346V/E348Q/M188K/D394W/S272L/E236K |
| M254F/E346V/E348Q/M188K/D394W/E236Q |
| M254F/E346V/E348Q/M188K/D394W/E236K |
| M254F/E346V/E348Q/M188K/D394W/E236D |
| M254F/E346V/E348Q/M188K/D394W/E236A |
| M188K/M254F/E346V/E348Q/D394W |

The present invention encompasses phenol oxidizing enzyme variants encoded by a polynucleotide sequence capable of hybridizing to the polynucleotide having the sequence as shown in SEQ ID NO:1 or SEQ ID NO:3 under conditions of intermediate to high stringency. In one embodiment, the variant enzymes of the invention are encoded by polynucleotides having at least 65% and less than 100% identity to the polynucleotide having the sequence as disclosed in SEQ ID NO:1 or SEQ ID NO:3. That is, the polynucleotides encoding the variant enzymes of this embodiment generally have at least 65% and less than 100%, at least 70% and less than 100%, at least 75% and less than 100%, at least 80% and less than 100%, at least 85% and less than 100%, at least 90% and less than 100%, or at least 95% and less than 100% identity to the polynucleotide having the sequence as disclosed in SEQ ID NO:1 or SEQ ID NO:3. Identity at the nucleic acid level is measured by the GAP program of the GCG Software (University Research Park, Madison, Wis.) with the following parameters. Gap Weight=50; Length Weight=4; Gap Creation Penalty=50; and Gap Extension Penalty=3.

In another embodiment, polynucleotides encoding the variant enzymes of the invention are derived from precursor polynucleotides having at least 65%, at least 70%, at least 75%, at least 80%, at least 85%, at least 90%, at least 95%, or 100% identity to the polynucleotide having the sequence as disclosed in SEQ ID NO:1 or SEQ ID NO:3. That is, such precursor polynucleotides are appropriately modified and then expressed to provide the phenol oxidizing enzyme variants of the invention.

The present invention also encompasses mutants, variants and derivatives, including portions, of the phenol oxidizing enzymes of the present invention as long as the mutant, variant or derivative phenol oxidizing enzyme is able to retain at least one characteristic activity of the naturally occurring phenol oxidizing enzyme.

Precursor Nucleic Acid Sequences

A nucleic acid sequence encoding a precursor phenol oxidizing enzyme can be isolated from an appropriate cell or microorganism using various methods well known in the art. According to one preferred embodiment herein, an appropriate cell or microorganism is one that includes a polynucleotide sequence which encodes a phenol oxidizing enzyme obtainable from *Stachybotrys* species which polynucleotide comprises between at least 65% and 100% identity, that is at least 65% identity, at least 70% identity, at least 75% identity, at least 80% identity, at least 85% identity, at least 90% identity and at least 95% identity to the polynucleotide sequence disclosed in SEQ ID NO:3, as long as the enzyme encoded by the polynucleotide is capable of modifying the color associated with colored compounds. In one embodiment, the phenol oxidizing enzyme has the polynucleotide sequence as shown in SEQ ID NO:3 or SEQ ID NO:1 or has the polynucleotide sequence as contained in *Stachybotrys chartarum* having MUCL accession number 38898. As will be understood by the skilled artisan, due to the degeneracy of the genetic code, a variety of polynucleotides can encode the phenol oxidizing enzyme disclosed in SEQ ID NO:2. The present invention encompasses all such polynucleotides.

The nucleic acid encoding a phenol oxidizing enzyme may be obtained by standard procedures known in the art from, for example, cloned DNA (e.g., a DNA "library"), by chemical synthesis, by cDNA cloning, by PCR, or by the cloning of genomic DNA, or fragments thereof, purified from a desired cell, such as a *Stachybotrys* species (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Nucleic acid sequences derived from genomic DNA may contain regulatory regions in addition to coding regions. Whatever the source, the isolated nucleic acid encoding a phenol oxidizing enzyme of the present invention can be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, and column chromatography.

Once nucleic acid fragments are generated, identification of the specific DNA fragment encoding a phenol oxidizing enzyme may be accomplished in a number of ways. For example, a phenol oxidizing enzyme encoding gene of the present invention or its specific RNA, or a fragment thereof, such as a probe or primer, may be isolated and labeled and then used in hybridization assays to detect a generated gene. (Benton, W. and Davis, R., 1977, *Science* 196: 180; Grunstein, M. And Hogness, D., 1975, *Proc. Natl. Acad. Sci. USA* 72:3961). Those DNA fragments sharing substantial sequence similarity to the probe will hybridize under high stringency conditions.

The present invention encompasses phenol oxidizing enzyme precursors obtainable from *Stachybotrys* species which are identified through nucleic acid hybridization techniques using SEQ ID NO:1 or SEQ ID NO:3 as a probe or primer and screening nucleic acid of either genomic or cDNA origin. Nucleic acid encoding phenol oxidizing enzymes obtainable from *Stachybotrys* species and having at least 65% identity to SEQ ID NO:1 or SEQ ID NO:3 can be detected by DNA—DNA or DNA-RNA hybridization or amplification using probes, portions or fragments of SEQ ID NO:1 or SEQ ID NO:3. Accordingly, the present invention provides a method for the detection of nucleic acid encoding a phenol oxidizing enzyme precursor by hybridizing part or all of a nucleic acid sequence of SEQ ID NO:1 or SEQ ID NO:3 with *Stachybotrys* nucleic acid of either genomic or cDNA origin.

Precursor nucleic acid sequences of the present invention include those sequences that are capable of hybridizing to the nucleotide sequence disclosed in SEQ ID NO:3 under conditions of intermediate to high stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego, Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. For example, in the present invention the following are the conditions for high stringency; hybridization was done at 37° C. in buffer containing 50% formamide, 5×SSPE, 0.5% SDS and 50 ug/ml of sheared Herring DNA. The washing was performed at 65° C. for 30 minutes in the presence of 1×SSC and 0.1% SDS once, at 65° C. for 30 minutes in presence of 0.5×SSC and 0.1% SDS once and at 65° C. for 30 minutes in presence of 0.1×SSC and 0.1% SDS once; the following are the conditions for intermediate stringency: hybridization was done at 37° C. in buffer containing 25% formamide, 5×SSPE, 0.5% SDS and 50 ug/ml of sheared Herring DNA. The washing was performed at 50° C. for 30 minutes in presence of 1×SSC and 0.1% SDS once, at 50° C. for 30 minutes in presence of 0.5×SSC and 0.1% SDS once; the following are the conditions for low stringency: hybridization was done at 37° C. in buffer containing 25% formamide, 5×SSPE, 0.5% SDS and 50 ug/ml of sheared Herring DNA. The washing was performed at 37° C. for 30 minutes in presence of 1×SSC and 0.1% SDS once, at 37° C. for 30 minutes in presence of 0.5×SSC and 0.1% SDS once. A nucleic acid capable of hybridizing to a nucleic acid probe under conditions of high stringency will have about 80% to 100% identity to the probe; a nucleic acid capable of hybridizing to a nucleic acid probe under conditions of intermediate stringency will have about 50% to about 80% identity to the probe.

The term "hybridization" as used herein includes "the process by which a strand of nucleic acid joins with a complementary strand through base pairing" (Coombs J (1994) Dictionary of Biotechnology, Stockton Press, New York, N.Y.).

The process of amplification as carried out in polymerase chain reaction (PCR) technologies is described in Dieffenback C W and G S Dveksler (1995, PCR Primer, a Laboratory Manual, Cold Spring Harbor Press, Plainview, N.Y.). A nucleic acid sequence of at least about 10 nucleotides and as many as about 60 nucleotides from SEQ ID NO:3 preferably about 12 to 30 nucleotides, and more preferably about 25 nucleotides can be used as a PCR primer.

A preferred method of isolating a nucleic acid sequence of the invention from a cDNA or genomic library is by use of polymerase chain reaction (PCR) using degenerate oligonucleotide probes prepared on the basis of the amino acid sequence of the protein having the amino acid sequence as shown in SEQ ID NO:2. For instance, the PCR may be carried out using the techniques described in U.S. Pat. No. 4,683,202.

Mutation of Precursor Nucleic Acid Sequences

Once a precursor-encoding DNA sequence has been selected, mutations may be introduced using any one or more of the methods known in the art.

In some situations, it may be desired to mutate the nucleic acid sequence using a site-directed technique. The site-directed mutagenesis of a DNA sequence encoding a precursor phenol oxidizing enzyme may be performed by use of any method known in the art. For example, mutations may be introduced using synthetic oligonucleotides. These oligonucleotides contain nucleotide sequences flanking the desired mutation sites; mutant nucleotides are inserted during oligonucleotide synthesis. In a specific method, a single-stranded DNA, bridging the oxidase-encoding sequence, is created in a vector carrying the oxidase gene. Then the synthetic nucleotide, bearing the desired mutation, is annealed to a homologous portion of the single-stranded DNA. The remaining gap is then filled in with taq DNA polymerase.

U.S. Pat. No. 4,760,025 discloses the introduction of oligonucleotides encoding multiple mutations by performing minor alterations of the cassette.

Another method of introducing mutations into laccase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

In some situations, it may be desired to introduce mutations into the nucleic acid sequence in a random fashion. The random mutagenesis of a DNA sequence encoding a precursor phenol oxidizing enzyme may conveniently be performed by use of any method known in the art. For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, for example, be one which induces transitions, transversions, inversions, scrambling, deletions, and/or insertions. Examples of a physical or chemical mutagenizing agent suitable for the present purpose include ultraviolet (UV) irradiation, hydroxylamine, N-methyl-N'-nitro-N-nitrosoguanidine (MNNG), 0-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the precursor enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that condons for unwanted amino acids are avoided. The doped or spiked oligonucleotide can be incorporated into the DNA encoding the phenol oxidizing enzyme by any published technique, using e.g. PCR, LCR or any DNA polymerase and ligase.

When PCR-generated mutagenesis is used, either a chemically treated or non-treated gene encoding a parent phenol oxidizing enzyme is subjected to PCR under conditions that increase the misincorporation of nucleotides (Deshler 1992; Leung et al., Technique, Vol. 1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the phenol oxidizing enzyme by, for example, transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the precursor phenol oxidizing enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of the cell or by being present on a vector harbored in the cell. Finally, the DNA to be mutagenized may be in isolated form. In one embodiment, the DNA sequence to be subjected to random mutagenesis is preferably a cDNA or a genomic cDNA sequence.

Expression Systems

The present invention provides host cells, expression methods and systems for the production of phenol oxidizing enzyme variants in host microorganisms, such as fungus, yeast and bacteria.

Once nucleic acid encoding a phenol oxidizing enzyme variant of the present invention is obtained, recombinant host cells containing the nucleic acid may be constructed using techniques well known in the art. Suitable hosts include, for example, fungal hosts such as *Aspergillus niger* or *Aspergillus oryzae.* Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Nucleic acid encoding a phenol oxidizing enzyme variant (e.g., DNA having between at least 65% and less than 100% identity to the nucleic acid of SEQ ID NO:1 or SEQ ID NO:3 as measured by the GAP program of the GCG Software (University Research Park, Madison, Wis.) with the following parameters; Gap Weight=50; Length Weight=4; Gap Creation Penalty=50; and Gap Extension Penalty=3) is obtained and transformed into a host cell using appropriate vectors. A variety of vectors and transformation and expression cassettes suitable for the cloning, transformation and expression in fungus, yeast and bacteria are known by those of skill in the art.

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phenol oxidizing enzymes in a host cell are known to those skilled in the art. Virtually any promoter capable of driving these phenol oxidizing enzyme is suitable for the present invention. Nucleic acid encoding the phenol oxidizing enzyme variant is linked operably through initiation codons to selected expression control regions for effective expression of the variant oxidative or reducing enzymes. Once suitable cassettes are constructed they are used to transform the host cell.

General transformation procedures are taught in Current Protocols in Molecular Biology (vol. 1, edited by Ausubel et al., John Wiley & Sons, Inc. 1987, Chapter 9) and include calcium phosphate methods, transformation using PEG and electroporation. For *Aspergillus* and *Trichoderma,* PEG and Calcium mediated protoplast transformation can be used (Finkelstein, DB 1992 Transformation. In Biotechnology of Filamentous Fungi. Technology and Products (eds. by Finkelstein & Bill) 113–156. Electroporation of protoplast is disclosed in Finkelestein, DB 1992 Transformation. In Biotechnology of Filamentous Fungi. Technology and Products (eds by Finkelstein & Bill) 113–156. Microprojection bombardment on conidia is described in Fungaro et al. (1995) Transformation of *Aspergillus nidulans* by microprojection bombardment on intact conidia. FEMS Microbiology Letters 125 293–298. *Agrobacterium* mediated transformation is disclosed in Groot et al. (1998) *Agrobacterium tumefaciens*-mediated transformation of filamentous fungi. Nature Biotechnology 16 839–842. For transformation of *Saccharomyces,* lithium acetate mediated transformation and PEG and calcium mediated protoplast transformation as well as electroporation techniques are known by those of skill in the art.

Host cells which contain the coding sequence for a phenol oxidizing enzyme variant of the present invention and express the protein may be identified by a variety of procedures known to those of skill in the art. These procedures include, but are not limited to, DNA—DNA or DNA-RNA hybridization and protein bioassay or immunoassay techniques which include membrane-based, solution-based, or chip-based technologies for the detection and/or quantification of the nucleic acid or protein.

Phenol Oxidizing Enzyme Activities

The phenol oxidizing enzyme variants of the present invention are capable of using a wide variety of different phenolic compounds as electron donors, while being very specific for molecular oxygen or hydrogen peroxide as the electron acceptor.

Depending upon the specific substrate and reaction conditions, e.g., temperature, presence or absence of enhancers, etc., each phenol oxidizing enzyme oxidation reaction will have an optimum pH.

Applications of Polyphenol Oxidizing Enzyme Variants

As described herein, the phenol oxidizing enzyme variants of the present invention are capable of oxidizing a wide variety of colored compounds having different chemical structures, using oxygen as the electron acceptor. Accordingly phenol oxidizing enzyme variants of the present invention can be used in applications where it is desirable to modify the color associated with colored compounds, such as in cleaning, e.g., for removing the food stains on fabric. In certain situations, a mediator or enhancer can be used to obtain desirable effects.

The phenol oxidizing enzyme variants of the present invention can be used in the field of textiles. For example, the phenol oxidizing enzyme variants of the present invention can be used in the treatment, processing, finishing, polishing, or production of fibers, or other fabrics or articles of manufacture. The enzyme variants herein can be useful, for example, in denim treatment (bleaching work-up processes); in de-coloring indigo waste; in fabric dyeing; in textile bleaching processes; in fiber modification; in achieving enhanced fiber or fabric properties; etc.

The phenol oxidizing enzyme variants of the present invention can be used in the leather industry. For example, the phenol oxidizing enzyme variants of the present invention can be used in the processing of animal hides including but not limited to de-hairing, liming, bating and/or tanning of hides.

The phenol oxidizing enzyme variants of the present invention can be used in the field of pulp and paper. For example, the phenol oxidizing enzyme variants of the present invention can be used in the manufacture of paper pulps and fluff pulps from raw materials such as wood, bamboo, and cereal rice straw; the manufacture of paper and boards for printing and writing, packaging, sanitary and other technical uses; recycling of cellulose fiber for the purpose of making paper and boards; and the treatment of waste products generated by and treated at pulp or paper mills and other facilities specifically dedicated to the manufacture of paper, pulp, or fluff. The enzyme variants herein can be useful, for example, in wood processing; in pulp bleaching; in wood fiber modification; in bio-glue (lignin activation) for MDF manufacturing; for enhanced paper properties; in ink removal; in paper dyeing; in adhesives (e.g. lignin based glue for particle- or fiber boards); etc.

The phenol oxidizing enzyme variants of the present invention can be used in the field of feed. For example, the phenol oxidizing enzyme variants of the present invention can be used as a feed additive alone or as part of a feed additive with the aim to increase the nutritional value of feed for any kind of animals such as chicken, cows, pigs, fish and pets; and/or as a processing aid to process plant materials and food industry by products with the aim to produce materials/products suitable as feed raw materials.

The phenol oxidizing enzyme variants of the present invention can be used in the field of contact lens cleaning.

For example, the phenol oxidizing enzyme variants of the present invention can be used in the cleaning, storage, disinfecting, and/or preservation of contact lens.

The phenol oxidizing enzyme variants of the present invention can be used in the field of starch. For example, the phenol oxidizing enzyme variants of the present invention can be used in the processing of a substrate including starch and/or grain to glucose (dextrose) syrup, fructose syrup or any other syrup, alcohol (potable or fuel) or sugar. Such starch processing may include processing steps such as liquefaction, saccharification, isomerization, and de-branching of a substrate.

The phenol oxidizing enzyme variants of the present invention can be used in the field of food. For example, the phenol oxidizing enzyme variants of the present invention can be used in the preparation, processing, or as an active ingredient in foods such as yellow fat, tea based beverages, culinary products, bakery, and frozen foods for human consumption. The phenol oxidizing enzyme variants of the present invention can be used, for example, as a bread improver, in food preservation, as an oxygen scavenger, etc.

The phenol oxidizing enzyme variants of the present invention can be used in the field of personal care. For example, the phenol oxidizing enzyme variants of the present invention can be used in the preparation of personal products for humans such as fragrances, and products for skin care, hair care, oral hygiene, personal washing and deodorant and/or antiperspirants, for humans. The enzyme variants herein can be useful, for example, in hair dyeing and/or bleaching, nails dyeing and/or bleaching; skin dyeing and/or bleaching; surface modification (e.g., as coupling reagent); as an anti-microbial agent; in odor removal; teeth whitening; etc.

The phenol oxidizing enzyme variants of the present invention can be used in the field of cleaning. For example, the phenol oxidizing enzyme variants of the present invention can be used in the cleaning, treatment or care of laundry items such as clothing or fabric; in the cleaning of household hard surfaces; in dishcare, including machine dishwashing applications; and in soap bars and liquids and/or synthetic surfactant bars and liquids. The enzyme variants herein can be useful, for example, in stain removal/de-colorization, and/or in the removal of odors, and/or in sanitization, etc.

The phenol oxidizing enzyme variants of the present invention can be used in the field of waste-water treatment. For example, the phenol oxidizing enzyme variants of the present invention can be used in decolorization of colored compounds; in detoxification of phenolic components; for anti-microbial activity (e.g., in water recycling); in bio-remediation; etc.

The phenol oxidizing enzyme variants of the present invention can be used in the field of bio-materials. For example, the phenol oxidizing enzyme variants of the present invention can be used as bio-catalysts for various organic reactions; and/or in connection with biopolymers; in connection with packaging; in connection with adhesives; in surface modification (activation and coupling agent); in production of primary alcohols; in connection with biosensors and/or organic syntheses; etc.

The phenol oxidizing enzyme variants of the present invention can be used in the field of anti-microbials. For example, the phenol oxidizing enzyme variants of the present invention can be used as an anti-microbial agent in cleaning compositions, or for reducing or eliminating the microbial load of various foods (e.g., meats) or feed.

Colored Compounds

In the present invention, a variety of colored compounds could be targets for oxidation by the phenol oxidizing enzyme variants taught herein. For example, in detergent applications, colored substances which may occur as stains on fabrics can be a target. Several types or classes of colored substances may appear as stains, such as prophyrin derived structures, such as heme in blood stain or chlorophyll in plants; tannins and polyphenols (see P. Ribéreau-Gayon, Plant Phenolics, Ed. Oliver & Boyd, Edinburgh, 1972, pp. 169–198) which occur in tea stains, wine stains, banana stains, peach stains; carotenoids, the coloured substances which occur in tomato (lycopene, red), mango (carotene, orange-yellow) (G. E. Bartley et al., The Plant Cell (1995), Vol 7, 1027–1038); anthocyanins, the highly colored molecules which occur in many fruits and flowers (P. Ribéreau-Gayon, Plant Phenolics, Ed. Oliver & Boyd, Edinburgh, 1972, 135–169); and Maillard reaction products, the yellow/brown colored substances which appear upon heating of mixtures of carbohydrate molecules in the presence of protein/peptide structures, such as found in cooking oil.

Enhancers

A phenol oxidizing enzyme variant of the present invention can act to modify the color associated with colored compounds in the presence or absence of enhancers depending upon the characteristics of the compound. If a colored compound is able to act as a direct substrate for the phenol oxidizing enzyme, the phenol oxidizing enzyme variant will modify the color associated with such compound in the absence of an enhancer, although an enhancer may still be preferred for optimum phenol oxidizing activity. For other colored compounds, unable to act as a direct substrate for the phenol oxidizing enzyme variant or not directly accessible to the variant, an enhancer is required for optimum phenol oxidizing activity and modification of the color.

Enhancers are described in for example WO 95/01426 published 12 Jan. 1995; WO 96/06930, published 7 Mar. 1996; and WO 97/11217 published 27 Mar. 1997. Enhancers includes but are not limited to phenothiazine-10-propionic acid (PTP), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis(3-ethylbenzothiazoline-6-sulfonate (ABTS).

Purification

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are fungal hosts such as *Aspergillus niger* or *Aspergillus oryzae*.

The phenol oxidizing enzyme variants of the present invention may be produced by cultivation of variant enzyme-producing *Stachybotrys* strains (such as *S. parvispora* MUCL 38996, *S. chartarum* MUCL 38898) under aerobic conditions in nutrient medium containing assimiable carbon and nitrogen together with other essential nutrient(s). The medium can be composed in accordance with principles well-known in the art.

During cultivation, the variant enzyme-producing strains secrete variant enzyme extracellularly. This permits the isolation and purification (recovery) of the variant enzyme to be achieved by, for example, separation of cell mass from a culture broth (e.g. by filtration or centrifugation). The resulting cell-free culture broth can be used as such or, if desired, may first be concentrated (e.g. by evaporation or ultrafiltration). If desired, the variant enzyme can then be separated from the cell-free broth and purified to the desired degree by conventional methods, e.g. by column chromatography.

The phenol oxidizing enzyme variants of the present invention can be isolated and purified from the culture broth into which they are extracellularly secreted by concentration of the supernatant of the host culture, followed by ammonium sulfate fractionation and gel permeation chromatography.

Small scale purification (e.g., <1 g) of variants can be performed using hydrophobic interaction chromatography. For example, samples, filtered over a 0.2 um filter, can be loaded onto a column containing 20 HP2 resin (Perceptives Biosystems), hooked up to a BioCad workstation (Perceptives Biosystems). The column can be washed with 35% of a 3M solution of ammonium sulfate in 30 mM Mes Bis Tris Propane buffer at pH 5.5. Elution of the phenol oxidizing enzyme activity can be performed using a salt gradient ranging from 25% to 0% of a 3M ammonium sulfate solution in 30 mM Mes Bis Tris Propane buffer at pH 5.5. The fractions enriched in phenol oxidizing enzyme activity can be monitored using UV absorbance at 280 nm and a qualitative ABTS activity assay. They can then be pooled, concentrated and diafiltered extensively against water. In experiments carried out in support of the present invention, phenol oxidizing enzyme samples purified according to this method are estimated to be at least about 70% pure.

The phenol oxidizing enzyme variants of the present invention may be formulated and utilized according to their intended application. In this respect, if being used in a detergent composition, the phenol oxidizing enzyme variant may be formulated, directly from the fermentation broth, as a coated solid using the procedure described in U.S. Pat. No. 4,689,297. Furthermore, if desired, the phenol oxidizing enzyme variant may be formulated in a liquid form with a suitable carrier. The phenol oxidizing enzyme variant may also be immobilized, if desired.

It should be appreciated that the present invention encompasses expression vectors and recombinant host cells comprising a phenol oxidizing enzyme variant of the present invention and the subsequent purification of the phenol oxidizing enzyme variant from the recombinant host cell.

Enzyme Compositions

A phenol oxidizing enzyme variant of the present invention may be used to produce, for example, enzymatic compositions for use in detergent or cleaning compositions; in textiles, that is in the treatment, processing, finishing, polishing, or production of fibers; in the production of paper and pulp; and in starch processing applications. Enzymatic compositions may also comprise additional components, such as, for example, for formulation or as performance enhancers.

For example, a detergent composition may comprise, in addition to one or more phenol oxidizing enzyme variants, conventional detergent ingredients such as surfactants, builders and further enzymes such as, for example, proteases, amylases, lipases, cutinases, cellulases or peroxidases. Other ingredients can include enhancers, stabilizing agents, bactericides, optical brighteners and/or perfumes. The enzymatic compositions may take any suitable physical form, such as a powder, an aqueous or non aqueous liquid, a paste or a gel.

Having thus described the phenol oxidizing enzyme variants of the present invention, the following examples are now presented for the purposes of illustration and are neither meant to be, nor should they be, read as being restrictive. Dilutions, quantities, etc. which are expressed herein in terms of percentages are, unless otherwise specified, percentages given in terms of percent weight per volume (w/v). As used herein, dilutions, quantities, etc., which are expressed in terms of % (v/v), refer to percentage in terms of volume per volume. Temperatures referred to herein are given in degrees centigrade (C). The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

EXAMPLE 1

Purification of a Precursor Phenol Oxidizing Enzyme

This example illustrates the purification of one preferred precursor phenol oxidizing enzyme obtainable from *Stachybotrys chartarum* and having the amino acid sequence as shown in SEQ ID NO:2.

*Stachybotrys chartarum* was grown on PDA plates (Difco) for about 5–10 days. A portion of the plate culture (about ¾x¾ inch) was used to inoculate 100 ml of PDB (potato dextrose broth) in 500-ml shake flask. The flask was incubated at 26–28 degrees C., 150 rpm, for 3–5 days until good growth was obtained.

The broth culture was then inoculated into 1 L of PDB in a 2,8-L shake flask. The flask was incubated at 26–28 degrees C., 150 rpm, for 2–4 days until good growth was obtained.

A 10-L fermentor containing a production medium was prepared containing in grams/liter the following components: glucose 15; lecithin 1.51; t-aconitic acid 1.73; $KH_2PO_4$ 3; $MgSO_4.7H_2O$ 0.8; $CaCl_2.2H_2O$ 0.1; ammonium tartrate 1.2; soy peptone 5; Staley 7359; benzyl alcohol 1; tween 20 1; nitrilotriacetic acid 0.15; $MnSO_4.7H_2O$ 0.05; NaCl 0.1; $FeSO_4.7H_2O$ 0.01; $CoSO_4$ 0.01; $CaCl_2.2H_2O$ 0.01; $ZnSO_4.7H_2O$ 0.01; $CuSO_4$ 0.001; $ALK(SO_4)2.12H_2O$ 0.001; $H_3BO_3$ 0.001; $NaMoO_4.2H_2O$ 0.001). The fermentor was then inoculated with the 1-L broth culture, and fermentation was conducted at 28 degrees C. for 60 hours, under a constant air flow of 5.0 liters/minute and a constant agitation of 120 RPM. The pH was maintained at 6.0.

The cells from one liter of broth were removed from the fermentation broth by centrifugation and the supernatant was further clarified by filtering through a DE filter. The low molecular weight salts were removed by diafiltration against 4 volumes of a buffer containing 20 mM MOPS adjusted to pH 7.0 using an Amicon YM10 membrane.

An ion exchange column containing 25 mls of Poros HQ-20 resin was used to purify the enzyme. The column was first equilibrated with 5 column volumes (125 mls) of 20 mM MOPS pH 7.0. Five mls of sample containing 5–10 mgs of total protein was loaded onto the column. The column was then washed with 3 column volumes of the MOPS buffer, then eluted with a gradient of 0–0.5M ammonium sulfate in a volume of 250 mls. The flow rate was 10 mls/min. Fractions were collected in 5 mls volumes. Each fraction was assayed for phenol oxidase activity using the ABTS method. The fractions that contained ABTS activity were subjected to electrophoresis on SDS PAGE. The bands on the gel that corresponded to the ABTS activity were cut out and the amino acid sequence was determined.

The data shown below is from another purification run and shows the presence of *Stachybotrys* phenol oxidase B band on an SDS PAGE. In this purification, crude material from the fermentation was purified on an ion exchange column using HQ20. The fractions were subjected to an initial non-denaturing (native) gel electrophoresis on a 4–20% Tris-Glycine gel. Samples were diluted with tracking dye and the running buffer was Laemmli buffer. This initial gel to look at purity was done on all fractions of the elution peak of interest and the resulting gel was silver stained. The second gel to confirm the active protein was done on every other fraction of the same peak and overlaid at pH7 and pH10 with ABTS. For the ABTS overlay, 4.5 mM ABTS was prepared at pH 7 and pH 10 (pH 7 with 50 mM sodium acetate and pH 10 with 50 mM sodium borate). The gel was divided into two parts for overlay: lanes 1–5 were overlaid with pH 7 and lanes 6–10 were overlaid with pH 10. Bands that were positive for ABTS were cut out and homogenized with Laemmli buffer and tracking dye containing BME. Samples were then placed at 100° C. for 5 minutes and loaded onto a Tris-glycine 4–20% gradient gel. The running buffer was Laemmli with 20% SDS. The gel was then silver stained.

Figure 8:
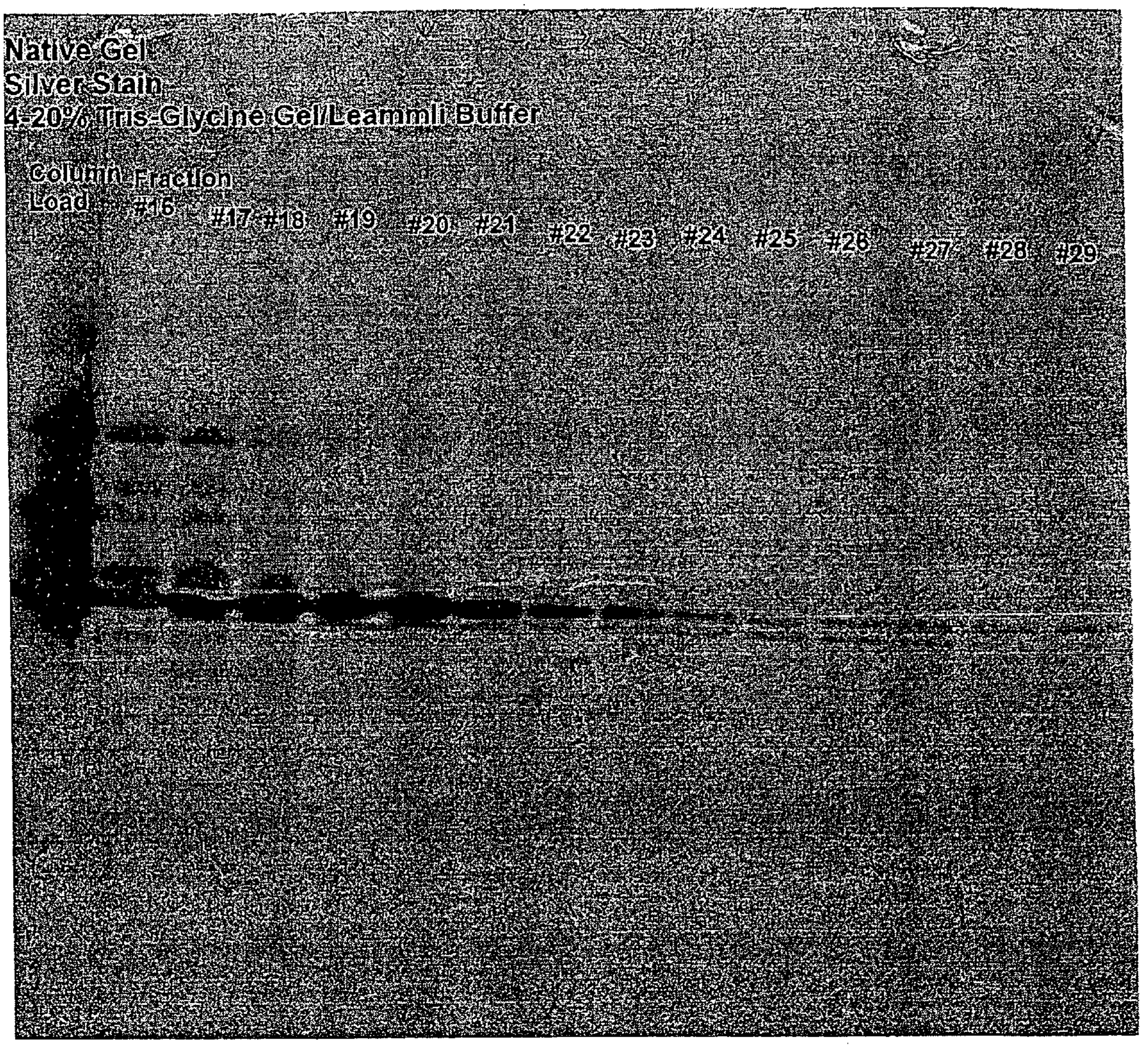
FIG. 8 shows a non-denatured (native) gel electrophoresis of *Stachybotrys chartarum* fractions from an ion exchange column (silver stained) as described in Example 1.
Figure 9:
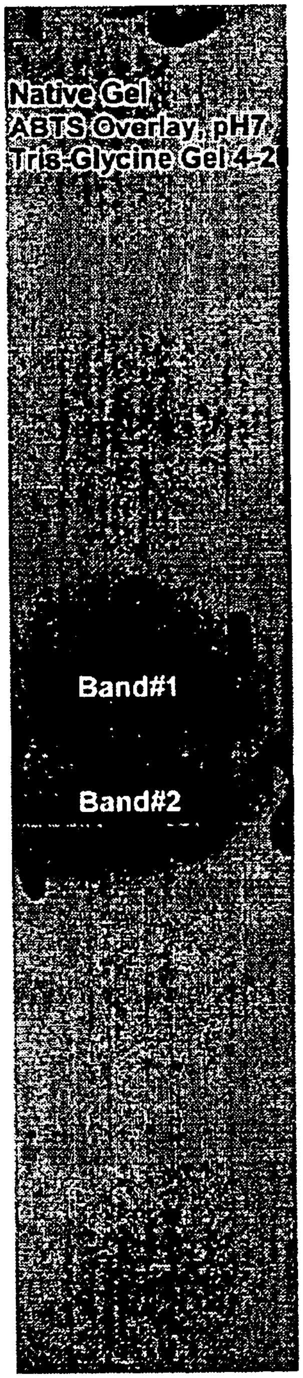
FIG. 9 shows a non-denatured gel electrophoresis of fractions with ABTS overlay as described in Example 1.
Figure 10:
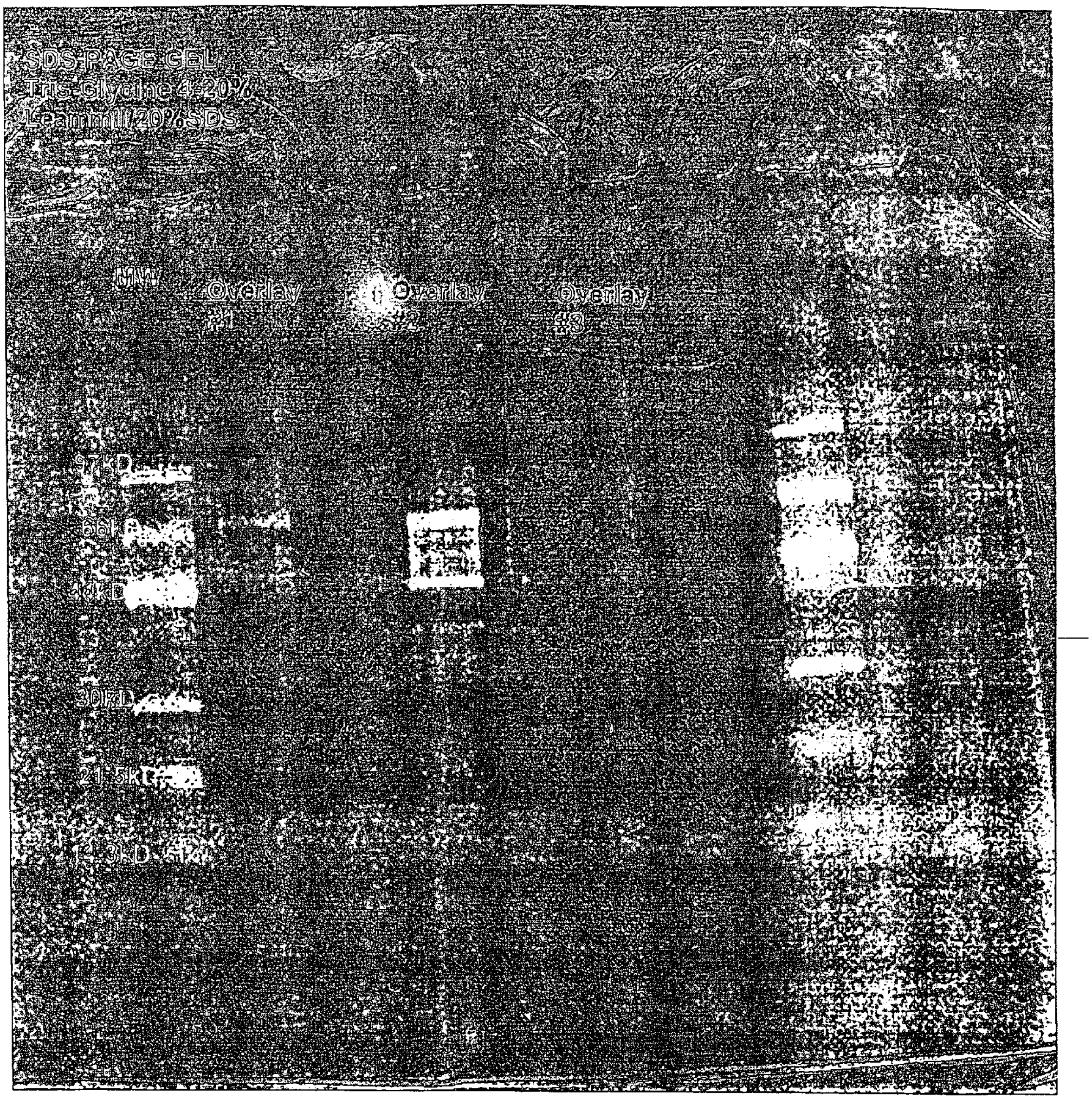
FIG. 10 shows an SDS-PAGE gel of bands identified and isolated from an ABTS overlay of the gel shown in FIG. 9. *Stachybotrys chartarum* phenol oxidase B is shown in the lane labeled Overlay 2. Lane Overlay 2 shows the observed banding pattern for *Stachybotrys chartarum* phenol oxidase B under the conditions described.

The results of the initial denaturing gel, the ABTS overlay gel and the SDS-PAGE gels are shown in FIGS. 8, 9 and 10, respectively.

EXAMPLE 2

Amino Acid Sequence Analysis of Precursor Phenol Oxidizing Enzyme

*Stachybotrys chartarum* phenol oxidizing enzyme prepared as disclosed in Example 1 was subjected to SDS polyacrylamide gel electrophoresis and isolated. The isolated fraction was treated with urea and iodoacetamide and digested by the enzyme endoLysC. The fragments resulting from the endoLysC digestion were separated via HPLC (reverse phase monobore C18 column, CH3CN gradient) and collected in a multititer plate. The fractions were analysed by MALDI for mass determination and sequenced via Edman degradation. The following amino acid sequences were determined and are shown in amino terminus to carboxy terminus orientation:

N' FVNSGENTSPNSVHLHGSFSR C' (SEQ ID No:5)

N' GVEPYEAAGLKDVVWLAR C' (SEQ ID No:6)

EXAMPLE 3

Cloning Genomic Nucleic Acid Encoding Precursor Phenol Oxidizing Enzyme

Two degenerated primers were designed based on the peptide sequences provided in Example 2. Primer 1 contains the following sequence: GTCAACAGTGGNGARAAYAC (SEQ ID No:7) and primer 2 contains the following sequence: GCGGCCTCATANGGCTCNAC (SEQ ID No:8) where N represents a mixture of all four nucleotides (A, T, C and G), R represents a mixture of A and G and Y represents a mixture of T and C.

For isolation of genomic DNA encoding a precursor phenol oxidizing enzyme, DNA isolated from *Stachybotrys chartarum* (MUCL #38898) was used as a template for PCR. The DNA was diluted 100 fold with Tris-EDTA buffer to a final concentration of 88 ng/ul. Ten microliters of diluted DNA was added to the reaction mixture which contained 0.2 mM of each nucleotide (A, G, C and T), 1× reaction buffer, 0.542 microgram of primer 1 and 0.62 microgram of primer 2 in a total of 100 microliter reaction in an eppendorf tube. After heating the mixture at 100° C. for 5 minutes, 2.5 units of Taq DNA polymerase was added to the reaction mix. The PCR reaction was performed at 95° C. for 1 minute, the primer was annealed to the template at 50° C. for 1 minute and extension was done at 72° C. for 1 minute. This cycle was repeated 30 times with an additional cycle of extension at 68° C. for 7 minutes. The PCR fragment detected by agarose gel contained a fragment of about 1.3 kilobase which was then cloned into the plasmid vector pCR-II (Invitrogen). The 1.3 kb insert was then subjected to nucleic acid sequencing. The sequence data revealed that it was the gene encoding *Stachybotrys chartarum* phenol oxidase B because the deduced peptide sequence matched the peptide sequences disclosed in Example 2 sequenced via Edman degradation. The PCR fragments containing the 5' gene and 3' gene were then isolated using the inverse PCR method with four primers deduced based on the sequence data from the 1.3 kb PCR fragment. FIG. 3 provides the full length genomic sequence (SEQ ID NO:3) of the *Stachybotrys* phenol oxidase B gene (spoB) including the promoter and terminator sequences.

EXAMPLE 4

Comparison with Other Oxidizing Enzymes

The translated protein sequence (shown on FIG. 2) (SEQ ID NO:2) was used as query to search DNA and protein databases. It showed that *Stachybotrys* oxidase B shared 67% identity of the bilirubin oxidase at the protein sequence level. FIG. 4 shows the sequence alignment of the two proteins using the GAP program of GCG software (University Research Park, Madison, Wis.) with following parameters: Gap Weight=12; Length Weight=4; Gap Creation Penalty=8; and Gap Extension Penalty=2.

EXAMPLE 5

Expression in *Aspergillus niger* var. *awamori*

Figure 6:
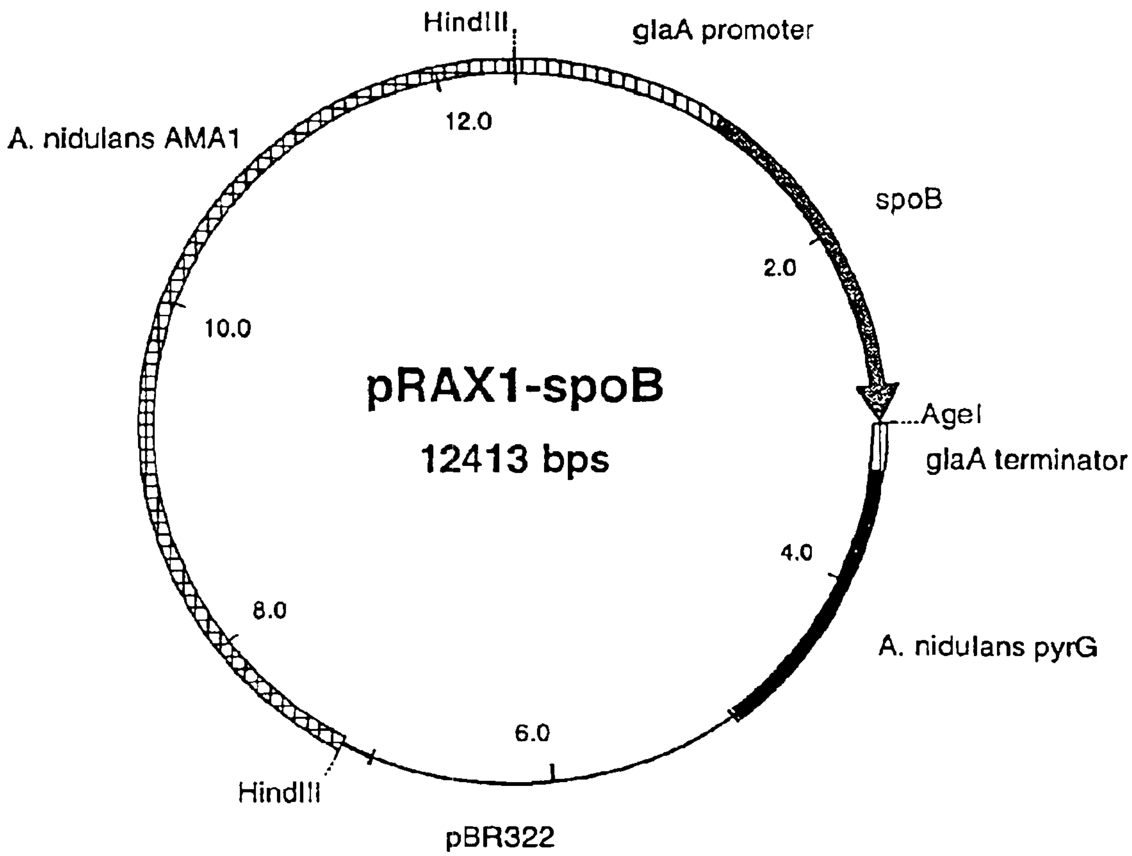
FIG. 6 is an illustration of expression of the *Stachybotrys* phenol oxidase B protein in a replicating plasmid. The *Stachybotrys* oxidase expression is under the *Aspergillus* glucoamylase promoter and terminator control. The transformation marker pyrG gene and the AMA 1 sequence are from *Aspergillus nidulans.*
Figure 7:
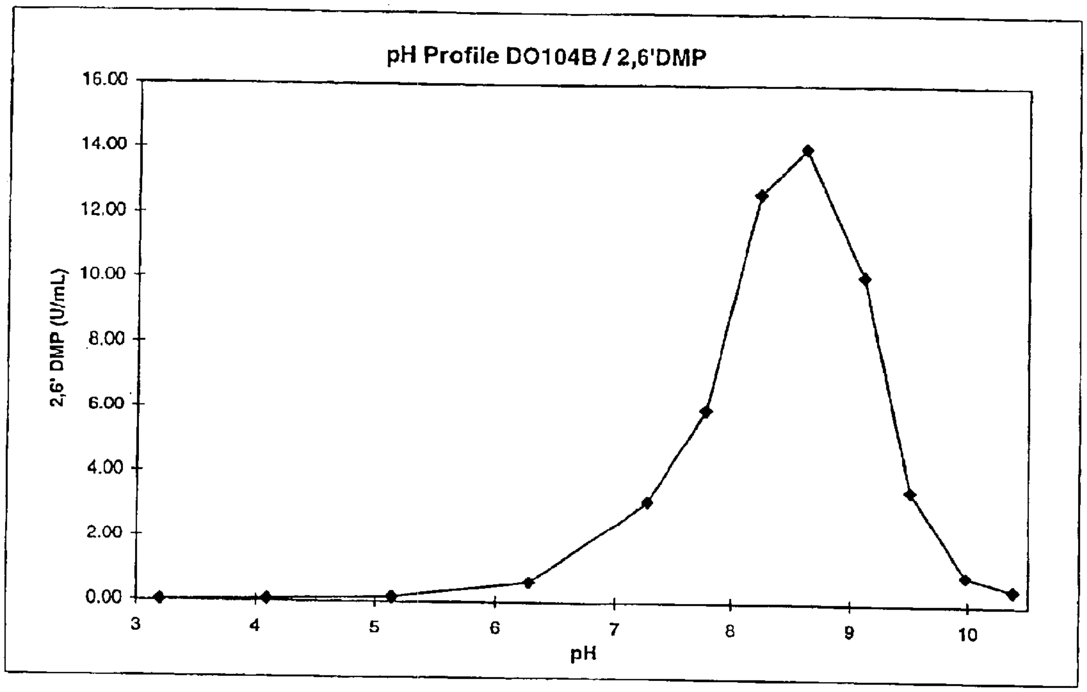
FIG. 7 shows the pH profile for *Stachybotrys* phenol oxidase B against the substrate 2.6 DMP.

The DNA fragment containing nucleic acid encoding the *Stachybotrys* phenol oxidizing enzyme B flanked by two newly introduced restriction enzyme sites (BamHI and AgeI) was isolated by PCR. This PCR fragment was first cloned into the plasmid vector pCR-II and subjected to nucleic acid sequencing to verify the gene sequence (FIG. 1). This DNA fragment was then cloned into the Bgl II to Age I site of vector (pGAPT2) to create a plasmid of pGAPT2-spoB, see FIG. 5. The expression plasmid was designed as pGAPT2-spoB (FIG. 5) which is capable of integrating into the host genome. The DNA fragment containing nucleic acid encoding the *Stachybotrys* phenol oxidizing enzyme flanked by two newly introduced restriction enzyme sites (BamHI and AgeI) was also cloned into the plasmid vector pRAX1 which is identical to the plasmid pGAPT2 except a 5259 bp HindIII fragment of *Aspergillus nidulans* genomic DNA fragment AMA1 sequence (Molecular Microbiology 1996 19:565–574) was inserted. The expression plasmid designated as pRAX1-spoB (FIG. 6), which is capable of being maintained as a replicating plasmid, was then transformed into *Aspergillus* strain GCAP4 (Gene 1990, 86:153–162) by standard PEG methods. A similar plasmid pGAPT-spoB was also constructed in which the pBR322 sequence of the pGAPT2-spoB plasmid (FIG. 5) was replaced by pUC18 DNA sequence. This plasmid was co-transformed with a pHELP1 plasmid (Current Genetics 1993, 24:520–524) in *Aspergillus* to generate transformants containing the replicating plasmid that expressing the mutants. Transformants were selected on plates without uridine. Three transformants were grown on -uridine plates for 3 days. The spores from transformants were resuspended in water with 0.01% tween80. The sports (100, 1000 or 10,000) were added to the 96 well microliter plates containing 160 ul of PROC medium. After 5 days growth at 30° C., these samples were shown to have ABTS activities. One thousand spores were added to 50 ml PROC medium in 250 ml shake flasks and after 3 days growth at 30° C., the ABTS activity was 0.33 units/ml. After 4 days growth at 30° C. activity, the ABTS activity was at 4.8 units/ml. About 1.2 million of spores were also added to one liter PROC medium in 2.8 liter shake flasks. Production of *Stachybotrys* phenol oxidase B protein reached 1 unit/ml at day 3 and 4 units/ml at day 4 and activity was detected in the ABTS assay.

EXAMPLE 6

Expression in *Trichoderma reesei*

The expression plasmid for use in transforming *Trichoderma reesei* was constructed as follows. The ends of the BamHI to AgeI fragment shown in FIG. 5 containing the gene encoding the *Stachybotrys* phenol oxidizing enzyme B were blunted by T4 DNA polymerase and inserted into PmeI restriction site of the *Trichoderma* expression vector, pTREX, a modified version of pTEX disclosed in PCT Publication No. WO 96/23928, which publication is herein incorporated by reference, which contains a CBHI promoter and terminater for gene expression and a *Trichoderma* pyr4 gene as a selection marker for transformants. The linear DNA fragment containing only the CBH1 promoter, the phenol oxidizing gene (spoB), the CHB1 terminater and selection marker pyr4 was isolated from a gel and was used to transform a uridine auxotroph strain of *Trichoderma reesei* (see U.S. Pat. No. 5,472,864) which has the four major cellulase genes deleted. Stable transformants were isolated on *Trichoderma* minimal plates without uridine. The transformants were grown on 50 ml of Proflo medium in shake flasks for 4 days at 28° C. to 30° C. and expression of the phenol oxidizing enzyme B was assayed by ABTS as described in Example 8. Proflo medium is composed of (g/l) Proflo 22.5; lactose 30.0; $(NH_4)_2SO_4$ 6.5 $KH_2PO_4$ 2.0; $MgSO_4$ 7 $H_2O$ 0.3; $CaCL_2$ 0.2; $CaCO_3$ 0.72; trace metal stock solution 1.0 ml/l and 10% Tween 80 2.0 ml/l. The trace metal stock solution used had (g/l) $FeSO_4.7H_2O$ 5.0; $MnSO_4.H_2O$ 1.6; $ZnSO_4.7H_2O$ 1.4; $CoCl_2.6H_2O$) 2.8.

EXAMPLE 7

Purification

The *Stachybotrys* phenol oxidase B culture broth obtained as described in Example 5 was withdrawn from the shake flask, cooled to 4° C., and centrifuged in a Sorval centrifuge for 15 minutes at 10,500 rpm using a GSA rotor. The resulting supernatant was then removed from the pellet and concentrated 6–10 fold by ultrafiltration using a TFF holder and cartridge UF from Millipore Corporation (6 ft^2 PTGC 10K polyethersulfone Cat.# CDUF006TG). The concentrate was washed with 4 volumes of Di water by diafiltration, resulting in a recovery yield between 40–80%. The material was then centrifuged again to remove the solids, and filtered through a 0.45 $\mu$ filter. The enzyme containing filtrate was then further purified using anion exchange column chromatography. In this regard, a Q-Sepharose anion exchange column was equilibrated with 50 mM potassium phosphate buffer, pH 6.9. Concentrate (enzyme mixture described above) was diluted 1 part to 4 parts (5 parts total) with 20 mM Potassium Phosphate buffer, pH 6.9 and loaded on the column at 120 mL/minute. The majority of contaminants were eluted with 20 mM Potassium Phosphate buffer, pH 6.9, containing 300 mM NaCl. Subsequently the column was eluted with the buffer containing 500 mM NaCl at a flow rate of 120 ml/minute. Respective fractions were then obtained. The respective fractions containing the highest phenol oxidizing enzyme activities were pooled together, concentrated and diafiltered to milli-Q using an Amicon concentrator with a YM10 membrane. Phenol oxidizing enzyme activity was then determined using the standard assay procedure based on the oxidation of ABTS, as described in Example 9. The enzyme activity so measured was 61.4 U/ml at pH5 and 6.1 U/mL at pH9.

EXAMPLE 8

Phenol Oxidizing Enzyme Variants

A large number of phenol oxidizing enzyme variants were produced using methods as disclosed herein and methods well known in the art.

Site-directed mutagenesis techniques employed included use of the QuikChange™ Site-Directed Mutagenesis Kit (Stratagene; La Jolla, Calif.). Random mutagenesis techniques employed included use of Epicurian Coli® XL1-Red Competent Cells (Stratagene; La Jolla, Calif.), as well as chemical mutagenesis using hydroxylamine.

The variants, which were derived from a *Stachybotrys* phenol oxidase B precursor (SEQ ID NO:2), include:

| |
|---|
| N391S |
| G115S |
| D562G |
| D394N/V425M |
| V134I/H177Y |
| L499F |
| M254F |
| M254F/L499F |
| M98L/M254F |
| L76W/M254F |
| M254F/F349Y |
| H175V |
| H177V |
| L76W/M254F/E302V |
| M254F/D394N/V425M |
| L76W/M254F/E302V/D394N/V425M |
| M254F/A296S |
| M254F/W318Y |
| M254F/L48Y |
| M254F/R83K |
| M254F/M188F |
| M254F/Q246H |
| M254F/S331T |
| M254F/V483T |
| M254F/R67T |
| V119L/M254F/N70V |
| M254F/N70V |
| M254F/D308S |
| M254F/E365T |
| M254F/S415A |
| M254F/R423A |
| M254F/D428G |
| M254F/R434E |
| M254F/E465M |
| M254F/A479G |
| M254F/N550A |
| P253A |
| V119L/M254F/A269M |
| M254F/A269M |
| V119L/M254F/G329N |

-continued

| |
|---|
| M254F/G329N |
| M254F/S331A |
| M254F/E346V/E348Q |
| V119L/M254F/E346V |
| M254F/E346V |
| V119L/M254F/A390P |
| M254F/A390P |
| M254F/N404T |
| V119L/M254F/S415L |
| M254F/S415L |
| M254F/R481G |
| M254F/A573N |
| M254F/A573N/F570L |
| M254F/L76W/E302V/M188K |
| M254N |
| M254L |
| M254A |
| M254I |
| M254E |
| M254S |
| M254H |
| M254V |
| M254T |
| M254P |
| M254G |
| M254K |
| M254C |
| M254F/D394G |
| M254F/D394V |
| M254F/D394S |
| M254F/D394H |
| M254F/D394P |
| M254F/D394Y |
| M254F/D394W |
| M254F/D394N |
| M254F/M179F |
| M254F/M179V |
| M254F/M179P |
| M254F/M179G |
| M254F/M179E |
| M254F/M179L |
| M254F/I181D |
| M254F/S180F/I181L |
| M254F/E346V/E302I |
| M254F/E346V/E302K |
| M254F/E346V/E348Q/E302F |
| M254F/E346V/E348Q/E302A |
| M254F/E346V/E348Q/E302L |
| M254F/E346V/E302C |
| M254F/E346V/E302V |
| M254F/E346V/M171T |
| M254F/E346V/E348Q/M171P |
| M254F/E346V/E348Q/M171L |
| M254F/E346V/M171Y |
| M254F/E346V/E348Q/M171V |
| M254F/E346V/M171S |
| M254F/E346V/M171R |
| M254F/E346V/E348Q/M171F |
| M254F/E346V/M171K |
| M254F/E346V/E348Q/M171Q |
| M254F/E346V/E348Q/M171N |
| M254F/E346V/E348Q/M171N/L172H |
| M254F/S272L |
| M254F/E236K |
| M254F/E346V/E348Q/M188K/D394W/S272L/E236K |
| M254F/E346V/E348Q/M188K/D394W/E236Q |
| M254F/E346V/E348Q/M188K/D394W/E236K |
| M254F/E346V/E348Q/M188K/D394W/E236D |
| M254F/E346V/E348Q/M188K/D394W/E236A |
| M188K/M254F/E346V/E348Q/D394W |

EXAMPLE 9

Assays Used in Determining Activity

9A. ABTS Assay

The ABTS assay is useful for determining phenol oxidizing activity. The ABTS assay is a spectrophotometric activity assay which uses the following reagents: assay buffer=50 mM sodium acetate, pH 5.0; and 4.5 mM ABTS (2,2'-azinobis 3 ethylbenzothiazoline-6-sulphonic acid) in distilled water.

0.75 ml assay buffer and 0.1 ml ABTS substrate solution are combined, mixed and added to a cuvette. A cuvette containing buffer-ABTS solution is used as a blank control. 0.05 ml of enzyme sample is added, rapidly mixed and placed into the cuvette containing buffer-ABTS solution. The rate of change in absorbance at 420 nm is measured, ΔOD 420/minute, for 15 seconds (longer than 15 seconds for samples having activity rates<0.1), in 2 second intervals, at 30° C. Enzyme samples having a high rate of activity are diluted with assay buffer to a level between 0.1 and 1.

The following calculation can then be carried out:

$$U/ml=(\Delta A_{420nm}/2)(\text{Dilution factor})$$

9B. Guaiacol Assay

The Guaiacol assay is also useful for determining phenol oxidizing activity, especially at higher pH levels. The following reagents are used: 50 mM Tris-HCl buffer pH 8.5 (To make 1L: dissolve 7.8 g of Tris-HCL in 1L of Dl water. Mix gently. Calibrate pH probes and adjust pH to 8.5. Buffer should be filter sterilized using a 0.2 um filter); 50 mM Guaiacol in Milli-Q-$H_2O$ (To make 20 mL of 50 mM Guaiacol: dissolve 124 uL of Guaiacol (Sigma catalog number 6-5502) in Milli-Q-$H_2O$. Guaiacol is light sensitive, solutions containing Guaiacol should be kept away from light by shielding container. This reagent solution should be made fresh daily for quality purposes).

The reagents are combined as follows:

| Guaiacol stock solution | final [conc] |
|---|---|
| 750 μL of pH 8.5 Tris-HCl 50 mM buffer | 42 mM Tris-HCl |
| 100 μL of 50 mM Guaiacol | 5.6 mM Guaiacol |

Enzyme sample is diluted in water, if necessary. 750 μL of Tris-HCl buffer, 100 μL of guaiacol, and 50 μL of enzyme are added to a disposable 1.5 mL cuvette. The reaction is allowed to proceed for 30 seconds at ambient room temperature of 21° C. and a reading is taken every 2 seconds using a spectrophotometer at a lambda of 470 nm. Before the first reading, mix the reaction solution well in the cuvette.

The following calculation can be carried out:

$$\text{Specific activity} = ((\Delta\text{OD units/min})/(0.050\text{ mL}))/([\text{protein}]\text{ mg/mL})$$

$$= \Delta\text{OD units/min/mg protein}$$

9C. TCA (Trichloroacetic Acid) Precipitation and Protein Determination

Protein concentration can be estimated, for example, using the BCA protein assay (See, e.g., Smith, P. K., et al (1985) "Measurement of protein using bicinchoninic acid." Anal. Biochem. 150: 76–85).

In an exemplary procedure, employing the Pierce BCA Protein Assay Reagent Kit (Product Cat. 23225) (Pierce; Rockford, Ill.) [Reference: Pierce Protein Assay Reagent Kit Instructions (for protein assay)]:

1) Prepare Pierce BCA Protein kit Working Reagent (WR):
   a) Mix 50 parts of Reagent A (Sodium carbonate, sodium bicarbonate, BCA detection reagent and sodium tartrate in 0.1 M NaOH) with 1 part of Reagent B (4% $CuSO_4.5H_2O$)

2) Prepare BSA std.s using 2 mg/mL BSA std. stock soln. See Mfrs. Instructions (diln.s prepared in Milli-Q water)

Chill 20% TCA throughly:

1) 50 uL of Sample/Std.s & 50 uL of 20% TCA>mix>put on ice for 20 min.
2) Centrifuge for 10 minutes>Decant>Dry in Speed Vac Speed Vac: Bring to speed>turn on vac.>run −2 min.>turn vac. off>stop and remove samples
3) Resuspend in 50 uL of WR
4) Add 1 mL WR to each tube
5) Incubate at 37° for 30 minutes
6) Cool to Rm. Temp. and read at $562_{nm}$ Plot Standards and Determine Protein Concentrations:

1) Do Scatter plot on Standards
2) Determine trend line
3) Display equation and $R^2$ value:
   use the equation to determine protein conc.: y=mx+b where: y=562 nm reading, and x=ug/mL Protein determination in connection with unpurified variants can be done by way of a different protocol; for example, the protein can be quantified via densitometry on Coomassie stained SDS gels.

EXAMPLE 10

Activity Determinations

10A. ABTS Activity

Using methods as described herein and as known in the art, the activity for ABTS was determined for several purified samples of the phenol oxidizing enzyme variants of Example 8:

| Activity for ABTS (purified protein) | Mutations |
|---|---|
| 30 u/mg | None (Wild Type) |
| 46 u/mg | D394N/V425M |
| 99 u/mg | M254F |
| 39 u/mg | M254F/E346V/E348Q |

Using methods as described herein and as known in the art, the activity for ABTS was determined for several unpurified samples of the phenol oxidizing enzyme variants of Example 8. The ABTS activity figures for unpurified mutants (in U/mg) were corrected for impurities. The protein concentrations were determined by protein gel.

| Activity for ABTS (unpurified protein) | Mutations |
|---|---|
| 42 u/mg | None (Wild Type) |
| 96 u/mg | M254F |
| 188 u/mg | M254F/L48Y |
| 97 u/mg | M254F/R83K |
| 96 u/mg | M254F/S331T |
| >110 u/mg | M254F/V483T |
| >104 u/mg | M254F/E465M |
| 48 u/ml | M254F/A479G |
| 173 u/mg | M254F/E346V |
| 58 u/mg | M254K |
| 172 u/mg | M254F/D394V |

-continued

| Activity for ABTS (unpurified protein) | Mutations |
|---|---|
| 45 u/mg | M254F/D394S |
| 43 u/mg | M254F/D394Y |
| 72 u/mg | M254F/M179F |
| 83 u/mg | M254F/M179V |
| 60 u/mg | M254F/M179G |
| 71 u/mg | M254F/M179E |
| 47 u/mg | M254F/M179L |
| 47 u/mg | M254F/S180F/I181L |

10B. Guaiacol Activity

The activity for Guaiacol was determined for a number of the phenol oxidizing enzyme variants of Example 8. The specific activity reported is based on Guaiacol activity that is corrected for the dilution of 50 μL of enzyme. The reported specific activity=((ΔOD units/min)/(0.050 mL))/([protein] mg/mL), thereby providing the specific activity as =ΔOD units/min/mg protein.

| Specific activity for Guaiacol (ΔOD/min/mg protein) | Mutations |
|---|---|
| 1.38 | DO104B (wild type "B" enzyme) |
| 4.54 | M254F |
| 3.92 | D394N/V425M |
| 2.49 | M254F/E346V/E348Q |
| 2.83 | M254F/S272L |
| 1.47 | L76W/M254F/E302V/D394N/V425M |
| 17.39 | M254F/E236K |
| 5.40 | M254S |
| 2.09 | M254F/S415L |
| 12.73 | M254N |
| 1.65 | L76W/M254F/E302V |
| 1.88 | M188K/M254F/E346V/E348Q/D394W |
| 6.27 | L76W/M188K/M254F/E302V |

EXAMPLE 11

Bleaching of Tomato Stains

The potential of the phenol oxidase enzyme variants to bleach stains was assessed by wash experiments, using a stain bleach monitor consisting of a tomato extract material that was prepared by acetone extraction of the chromophores from concentrated tomato paste. For the preparation of the stains, the colored acetone solution was applied to cotton swatches.

The experiments were performed in small 250 ml containers, to which 15 ml of wash solution were added. Purified phenol oxidizing enzyme was added to the wash solution at 15 mg/l.

The enhancer phenothiazine-10-propionate (β(10-phenothiazinyl)propionic acid) was dosed at 250 μM. The following formulation, set at pH 9, was used as wash solution (2 g/l):

| | |
|---|---|
| Linear Alkylbenzene Sulphonate | 24% |
| Sodium tripolyphosphate | 14.5% |
| Soda ash | 17.5% |
| Sodium Silicate | 8.0% |

-continued

| | |
|---|---|
| SCMC | 0.37% |
| Blue pigment | 0.02% |
| Moisture/salts | 34.6% |

The swatches were washed during 30 minutes at 30° C. After the wash, the swatches were tumble-dried and the reflectance spectra were measured using a Minolta spectrometer. The colors of the swatch after the wash, and of clean fabric, were expressed in the CIELAB L*a*b* color space. In this color space, L* indicates lightness and a* and b* are the chromaticity coordinates. Color differences between two swatches are expressed as ΔE, which is calculated from the following equation:

$$\Delta E=\sqrt{\Delta L^2+\Delta\alpha^2+\Delta b^2}$$

The results, as ΔE values, are shown in Table 1 below. As the color difference is measured between the residual stain after the wash and clean fabric, a lower ΔE means improved stain removal.

| Condition/mutation | ΔE |
|---|---|
| Enhancer, without enzyme | 35.6 |
| Wild type | 27.95 |
| M254F | 25.27 |
| D394N/V425M | 23.86 |
| M254F/E346V/E348Q | 18.27 |

Clearly, the enzyme variants deliver improved stain removal.

It is claimed:

1. An isolated polynucleotide encoding an enzymatically active variant of a phenol oxidizing enzyme, wherein said phenol oxidizing enzyme has the amino acid sequence as disclosed in SEQ ID NO:2, said variant comprising a sequence that differs from that of said phenol oxidizing enzyme in at least one of the positions 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573, or sequence positions corresponding thereto.

2. An expression vector comprising the polynucleotide of claim 1.

3. A host cell comprising the expression vector of claim 2.

4. The host cell of claim 3, wherein said host cell is a filamentous fungus.

5. The host cell of claim 4, wherein said fungus is an *Aspergillus* species or a *Trichoderma* species.

6. A method for obtaining a phenol oxidizing enzyme variant from a *Stachybotrys* species, comprising the steps of:

mutagenizing a gene encoding a phenol oxidizing enzyme, which phenol oxidizing enzyme comprises an amino acid sequence having the amino acid sequence shown in SEQ ID NO:2;

introducing the mutant gene into a host strain whereby a transformed host strain is obtained;

growing said transformed host whereby said mutant gene is expressed and a phenol oxidizing enzyme variant, differing from said phenol oxidizing enzyme by one or more amino acid substitutions, is identified by recovering said variant and screening it for increased phenol oxidizing activity and/or increased pH optimum.

7. The method of claim 6, wherein said one or more amino acid substitutions correspond to amino acid positions selected from the group consisting of 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573 of said SEQ ID NO:2 sequence.

8. The method of claim 6, wherein said mutagenized gene is a cloned *Stachybotrys* gene.

9. A method for producing a variant of a phenol oxidizing enzyme, which enzyme comprises the amino acid sequence shown in SEQ ID NO:2; said method comprising the steps of:

(a) culturing a host cell comprising a polynucleotide encoding said variant, wherein said variant differs from said phenol oxidizing enzyme sequence in at least one of the positions 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573, or sequence positions corresponding thereto, under conditions suitable for the production of said variant; and (b) optionally recovering said variant produced.

10. The isolated polynucleotide of claim 1, wherein said polynucleotide encodes a variant which comprises a sequence that differs from that of the phenol oxidizing enzyme in at least one of the positions 254, 272, 346, 348, 394, and 425, or sequence positions corresponding thereto.

11. The isolated polynucleotide of claim 1 wherein said polynucleotide encodes an amino acid substitution at one or more of the positions or position sets: 76/254/302; 76/254/302/188; 76/254/302/394/425; 119/254/329; 119/254/390; 119/254/415; 171/254/346; 236/254; 254; 254/272; 254/302/346/348; 254/346/348; 254/394; 254/550; and 394/425.

12. The isolated polynucleotide of claim 1 encoding a variant having at least one amino acid substitution or substitution set selected from:

N391S
G115S
D562G
D394N/V425M
V134I/H177Y
L499F
M254F
M254F/L499F
M98L/M254F
L76W/M254F
M254F/F349Y
H175V
H177V
L76W/M254F/E302V
M254F/D394N/V425M
L76W/M254F/E302V/D394N/V425M
M254F/A296S
M254F/W318Y
M254F/148Y
M254F/R83K
M254F/M188F
M254F/Q246H
M254F/S331T
M254F/V483T
M254F/R67T
V119L/M254F/N70V
M254F/N70V
M254F/D308S
M254F/E365T
M254F/S415A
M254F/R423A
M254F/D428G
M254F/R434E
M254F/E465M
M254F/M79G
M254F/N550A
P253A
V119L/M254F/A269M
M254F/A269M
V119L/M254F/G329N
M254F/G329N
M254F/S331A
M254F/E346V/E348Q
V119L/M254F/E346V
M254F/E346V
V119L/M254F/A390P
M254F/A390P
M254F/N404T
V119L/M254F/S415L
M254F/S415L
M254F/R481G
M254F/A573N
M254F/A573N/F570L
M254F/L76W/E302V/M188K
M254N
M254L
M254A
M254I
M254E
M254S
M254H
M254V
M254T
M254P
M254G
M254K
M254C
M254F/D394G
M254F/D394V
M254F/D394S

-continued

| |
|---|
| M254F/D394H |
| M254F/D394P |
| M254F/D394Y |
| M254F/D394W |
| M254F/D394N |
| M254F/M179F |
| M254F/M179V |
| M254F/M179P |
| M254F/M179G |
| M254F/M179E |
| M254F/M179L |
| M254F/181D |
| M254F/S180F/I181L |
| M254F/E346V/E302I |
| M254F/E346V/E302K |
| M254F/E346V/E348Q/E302F |
| M254F/E346V/E348Q/E302A |
| M254F/E346V/E348Q/E302L |
| M254F/E346V/E302C |
| M254F/E346V/E302V |
| M254F/E346V/M171T |
| M254F/E346V/E348Q/M171P |
| M254F/E346V/E348Q/M171L |
| M254F/E346V/M171Y |
| M254F/E346V/E348Q/M171V |
| M254F/E346V/M171S |
| M254F/E346V/M171R |
| M254F/E346V/E348Q/M171F |
| M254F/E346V/M171K |
| M254F/E346V/E348Q/M171Q |
| M254F/E346V/E348Q/M171N |
| M254F/E346V/E348Q/M171N/L172H |
| M254F/S272L |
| M254F/E236K |
| M254F/E346V/E348Q/M188K/D394W/S272L/E236K |
| M254F/E346V/E348Q/M188K/D394W/E236Q |
| M254F/E346V/E348Q/M188K/D394W/E236K |
| M254F/E346V/E348Q/M188K/D394W/E236D |
| M254F/E346V/E348Q/M188K/D394W/E236A |
| M188K/M254F/E346V/E348Q/D394W |

13. The isolated polynucleotide of claim 1, 10, 11 or 12, wherein the phenol oxidizing enzyme has the amino acid sequence disclosed in SEQ ID NO:2.

14. The isolated polynucleotide of claim 1, wherein the phenol oxidizing enzyme variant has increased phenol oxidizing activity at high pH.

15. The isolated polynucleotide of claim 14, wherein the variant has a pH optimum of at least 8.

16. The isolated polynucleotide of claim 1, wherein said phenol oxidizing enzyme is obtainable from a *Stachybotrys* species.

17. The method according to claim 8, wherein said cloned *Stachybotrys chartarum* gene is a cloned *Stachybotrys chartarum* gene or a cloned gene capable of hybridizing to such a *Stachybotrys* gene under conditions of intermediate to high stringency.

18. The method according to claim 15, wherein the variant has a pH of at least 9.

19. The method according to claim 16, wherein the *Stachybotrys* species is *Stachybotrys chartarum*.

* * * * *

UNITED STATES PATENT AND TRADEMARK OFFICE

CERTIFICATE OF CORRECTION

PATENT NO. : 6,905,853 B1
DATED : June 14, 2005
INVENTOR(S) : Huaming Wang

It is certified that error appears in the above-identified patent and that said Letters Patent is hereby corrected as shown below:

Column 42,
Line 25, should be -- M254F/L48Y --.

Signed and Sealed this

First Day of November, 2005

JON W. DUDAS
*Director of the United States Patent and Trademark Office*

SEQUENCE LISTING

<160> NUMBER OF SEQ ID NOS: 8

<210> SEQ ID NO 1
<211> LENGTH: 1958
<212> TYPE: DNA
<213> ORGANISM: Stachybotrys chartarum

<400> SEQUENCE: 1
ggatccatca acatgatcag ccaagctatc ggagccgtgg ctctgggcct tgctgtgatc 60
ggcggcagct ctgtcgatgc cagatccgtt gctggtcgat cgacagacat gccttccggt 120
ctcaccaaga ggcagacgca gctgagtcct cccctggcct tgtacgaagt gcctctgccg 180
atccctcctc tgaaggcgcc caagtagtaa gtacattcta taggctagca gagccaacgt 240
tgctaatcat tgcagtaccg tccccaaccc caacactgga gaggacatct tgtactacga 300
gatggagatt aggcccttct cccaccagat ctaccctgat ctggagccgg ccaacatggt 360
tggatacgat ggcatgtccc caggacctac catcatcgtt cctcgtggca ctgagagtgt 420
tgtccgcttc gtgaacagcg gagagaacac ctctcccaac agcgtccact tgcacggctc 480
tttctctcga gctccctttg atggttgggc tgaggacact acccagcctg gcgagtacaa 540
ggattactac taccccaaca ggcaggctgc ccgcatgctt tggtaccatg accatgccat 600
gtccatcacc gccgagaacg cctacatggg tcaggctggt gtctacatga tccaggaccc 660
ggctgaggat gccctgaacc tccccagcgg ctacggcgag tttgatatcc ccttggttct 720
gactgccaag cgatacaacg cagacggcac tctcttctcc accaatggag aggtttccag 780
cttctggggt gacgttattc aagtggtaag ttgagcccat tgagatgctt cagatcctag 840
aagtatcgat gtatgaaatt gtgcatgctc taaccagtgc tatcacagaa cggtcagcct 900
tggcctatgc tcaacgtgca gccgcgcaag taccgcttcc gcttcctcaa cgctgccgtc 960
tcacgctctt tcgctctgta tcttgctacc tctgaggatt cagagaccag acttcccttc 1020
caggtcattg ccgctgacgg tggtctgctt gagggccctg ttgacactga cactctgtac 1080
atctctatgg ccgagcgctg ggaggttgtt atcgacttct ccaccttcgc tggccagtcc 1140
atcgatatcc gcaaccttcc tggtgctgac ggtctcggtg ttgagcctga gtttgataac 1200
actgacaagg tcatgcgatt cgtcgttgat gaagtccttg agtcgcccga cacttctgag 1260
gtgcctgcca acctccgaga tgttcctttc cccgagggcg gcaactggga ccccgcaaac 1320

-continued

```
cccactgatg acgagacttt caccttcggc cgtgctaatg gacagtggac aatcaacgga   1380

gttaccttct cggatgtcga gaaccgtctg ctccgcaatg tgccccgcga cactgttgag   1440

atctggcgac ttgagaacaa ctccaacggt tggactcacc ctgttcacat tcacctcgtt   1500

gacttccgag tcctttctcg ttccactgcc cgtggagtcg agccttatga ggctgctggt   1560

ctcaaggatg ttgtctggct ggctcgtcgt gaggttgtct atgttgaggc ccactacgct   1620

cctttcccgt aagttctcgc cttttaccta actggttttc actcatgcta acatctacaa   1680

gtggtgtcta catgttgcac tgccacaacc tgatccacga ggaccacgac atgatggctg   1740

ctttcaatgt cactgttctc ggtgactatg gctacaacta caccgagttc attgacccca   1800

tggagcctct ctggaggccc cgccccttcc tcctcggaga gttcgagaat ggctcgggtg   1860

acttcagcga gcttgccatc actgaccgca ttcaggagat ggctagcttc aacccctacg   1920

cccaggctga tgatgatgcc gctgaggagt agaccggt                          1958
```

```
<210> SEQ ID NO 2
<211> LENGTH: 583
<212> TYPE: PRT
<213> ORGANISM: Stachybotrys chartarum

<400> SEQUENCE: 2

Met Ile Ser Gln Ala Ile Gly Ala Val Ala Leu Gly Leu Ala Val Ile
 1               5                  10                  15

Gly Gly Ser Ser Val Asp Ala Arg Ser Val Ala Gly Arg Ser Thr Asp
            20                  25                  30

Met Pro Ser Gly Leu Thr Lys Arg Gln Thr Gln Leu Ser Pro Pro Leu
        35                  40                  45

Ala Leu Tyr Glu Val Pro Leu Pro Ile Pro Pro Leu Lys Ala Pro Asn
    50                  55                  60

Thr Val Pro Asn Pro Asn Thr Gly Glu Asp Ile Leu Tyr Tyr Glu Met
65                  70                  75                  80

Glu Ile Arg Pro Phe Ser His Gln Ile Tyr Pro Asp Leu Glu Pro Ala
                85                  90                  95

Asn Met Val Gly Tyr Asp Gly Met Ser Pro Gly Pro Thr Ile Ile Val
            100                 105                 110

Pro Arg Gly Thr Glu Ser Val Val Arg Phe Val Asn Ser Gly Glu Asn
        115                 120                 125

Thr Ser Pro Asn Ser Val His Leu His Gly Ser Phe Ser Arg Ala Pro
    130                 135                 140

Phe Asp Gly Trp Ala Glu Asp Thr Thr Gln Pro Gly Glu Tyr Lys Asp
145                 150                 155                 160

Tyr Tyr Tyr Pro Asn Arg Gln Ala Ala Arg Met Leu Trp Tyr His Asp
                165                 170                 175

His Ala Met Ser Ile Thr Ala Glu Asn Ala Tyr Met Gly Gln Ala Gly
            180                 185                 190

Val Tyr Met Ile Gln Asp Pro Ala Glu Asp Ala Leu Asn Leu Pro Ser
        195                 200                 205

Gly Tyr Gly Glu Phe Asp Ile Pro Leu Val Leu Thr Ala Lys Arg Tyr
    210                 215                 220

Asn Ala Asp Gly Thr Leu Phe Ser Thr Asn Gly Glu Val Ser Ser Phe
225                 230                 235                 240

Trp Gly Asp Val Ile Gln Val Asn Gly Gln Pro Trp Pro Met Leu Asn
                245                 250                 255

Val Gln Pro Arg Lys Tyr Arg Phe Arg Phe Leu Asn Ala Ala Val Ser
```

-continued

```
        260                 265                 270

Arg Ser Phe Ala Leu Tyr Leu Ala Thr Ser Glu Asp Ser Glu Thr Arg
    275                 280                 285

Leu Pro Phe Gln Val Ile Ala Ala Asp Gly Gly Leu Leu Glu Gly Pro
    290                 295                 300

Val Asp Thr Asp Thr Leu Tyr Ile Ser Met Ala Glu Arg Trp Glu Val
305                 310                 315                 320

Val Ile Asp Phe Ser Thr Phe Ala Gly Gln Ser Ile Asp Ile Arg Asn
                325                 330                 335

Leu Pro Gly Ala Asp Gly Leu Gly Val Glu Pro Glu Phe Asp Asn Thr
            340                 345                 350

Asp Lys Val Met Arg Phe Val Val Asp Glu Val Leu Glu Ser Pro Asp
        355                 360                 365

Thr Ser Glu Val Pro Ala Asn Leu Arg Asp Val Pro Phe Pro Glu Gly
    370                 375                 380

Gly Asn Trp Asp Pro Ala Asn Pro Thr Asp Asp Glu Thr Phe Thr Phe
385                 390                 395                 400

Gly Arg Ala Asn Gly Gln Trp Thr Ile Asn Gly Val Thr Phe Ser Asp
                405                 410                 415

Val Glu Asn Arg Leu Leu Arg Asn Val Pro Arg Asp Thr Val Glu Ile
            420                 425                 430

Trp Arg Leu Glu Asn Asn Ser Asn Gly Trp Thr His Pro Val His Ile
        435                 440                 445

His Leu Val Asp Phe Arg Val Leu Ser Arg Ser Thr Ala Arg Gly Val
    450                 455                 460

Glu Pro Tyr Glu Ala Ala Gly Leu Lys Asp Val Val Trp Leu Ala Arg
465                 470                 475                 480

Arg Glu Val Val Tyr Val Glu Ala His Tyr Ala Pro Phe Pro Gly Val
                485                 490                 495

Tyr Met Leu His Cys His Asn Leu Ile His Glu Asp His Asp Met Met
            500                 505                 510

Ala Ala Phe Asn Val Thr Val Leu Gly Asp Tyr Gly Tyr Asn Tyr Thr
        515                 520                 525

Glu Phe Ile Asp Pro Met Glu Pro Leu Trp Arg Pro Arg Pro Phe Leu
    530                 535                 540

Leu Gly Glu Phe Glu Asn Gly Ser Gly Asp Phe Ser Glu Leu Ala Ile
545                 550                 555                 560

Thr Asp Arg Ile Gln Glu Met Ala Ser Phe Asn Pro Tyr Ala Gln Ala
                565                 570                 575

Asp Asp Asp Ala Ala Glu Glu
            580


<210> SEQ ID NO 3
<211> LENGTH: 2095
<212> TYPE: DNA
<213> ORGANISM: Stachybotrys chartarum

<400> SEQUENCE: 3

cagctcggtc tactactctc gcttctcttt gacaaatcaa atctaccaat cgttccttca      60

atttcaaacg atcaacatga tcagccaagc tatcggagcc gtggctctgg gccttgctgt     120

gatcggcggc agctctgtcg atgccagatc cgttgctggt cgatcgacag acatgccttc     180

cggtctcacc aagaggcaga cgcagctgag tcctcccctg gccttgtacg aagtgcctct     240

gccgatccct cctctgaagg cgcccaagta gtaagtacat tctataggct agcagagcca     300
```

-continued

```
acgttgctaa tcattgcagt accgtcccca accccaacac tggagaggac atcttgtact    360
acgagatgga gattaggccc ttctcccacc agatctaccc tgatctggag ccggccaaca    420
tggttggata cgatggcatg tccccaggac ctaccatcat cgttcctcgt ggcactgaga    480
gtgttgtccg cttcgtgaac agcggagaga acacctctcc caacagcgtc cacttgcacg    540
gctctttctc tcgagctccc tttgatggtt gggctgagga cactacccag cctggcgagt    600
acaaggatta ctactacccc aacaggcagg ctgcccgcat gctttggtac catgaccatg    660
ccatgtccat caccgccgag aacgcctaca tgggtcaggc tggtgtctac atgatccagg    720
acccggctga ggatgccctg aacctcccca gcggctacgg cgagtttgat atccccttgg    780
ttctgactgc caagcgatac aacgcagacg gcactctctt ctccaccaat ggagaggttt    840
ccagcttctg ggtgacgtt attcaagtgg taagttgagc ccattgagat gcttcagatc    900
ctagaagtat cgatgtatga aattgtgcat gctctaacca gtgctatcac agaacggtca    960
gccttggcct atgctcaacg tgcagccgcg caagtaccgc ttccgcttcc tcaacgctgc   1020
cgtctcacgc tctttcgctc tgtatcttgc tacctctgag gattcagaga ccagacttcc   1080
cttccaggtc attgccgctg acggtggtct gcttgagggc cctgttgaca ctgacactct   1140
gtacatctct atggccgagc gctgggaggt tgttatcgac ttctccacct tcgctggcca   1200
gtccatcgat atccgcaacc ttcctggtgc tgacggtctc ggtgttgagc ctgagtttga   1260
taacactgac aaggtcatgc gattcgtcgt tgatgaagtc cttgagtcgc ccgacacttc   1320
tgaggtgcct gccaacctcc gagatgttcc tttccccgag ggcggcaact gggaccccgc   1380
aaaccccact gatgacgaga ctttcacctt cggccgtgct aatggacagt ggacaatcaa   1440
cggagttacc ttctcggatg tcgagaaccg tctgctccgc aatgtgcccc gcgacactgt   1500
tgagatctgg cgacttgaga acaactccaa cggttggact caccctgttc acattcacct   1560
cgttgacttc cgagtccttt ctcgttccac tgcccgtgga gtcgagcctt atgaggctgc   1620
tggtctcaag gatgttgtct ggctggctcg tcgtgaggtt gtctatgttg aggcccacta   1680
cgctcctttc ccgtaagttc tcgcctttta cctaactggt tttcactcat gctaacatct   1740
acaagtggtg tctacatgtt gcactgccac aacctgatcc acgaggacca cgacatgatg   1800
gctgctttca atgtcactgt tctcggtgac tatggctaca actacaccga gttcattgac   1860
cccatggagc ctctctggag gccccgcccc ttcctcctcg gagagttcga gaatggctcg   1920
ggtgacttca gcgagcttgc catcactgac cgcattcagg agatggctag cttcaacccc   1980
tacgcccagg ctgatgatga tgccgctgag gagtaaatat gatgatcgtc gaatgattta   2040
tggacagcag tatatagcta ttttaggaaa tacttgaata agttgtggtg cttaa        2095
```

<210> SEQ ID NO 4
<211> LENGTH: 572
<212> TYPE: PRT
<213> ORGANISM: Myrothecium verucaria

<400> SEQUENCE: 4

```
Met Phe Lys His Thr Leu Gly Ala Ala Ala Leu Ser Leu Leu Phe Asn
 1               5                  10                  15

Ser Asn Ala Val Gln Ala Ser Pro Val Pro Glu Thr Ser Pro Ala Thr
            20                  25                  30

Gly His Leu Phe Lys Arg Val Ala Gln Ile Ser Pro Gln Tyr Pro Met
        35                  40                  45

Phe Thr Val Pro Leu Pro Ile Pro Pro Val Lys Gln Pro Arg Leu Thr
```

-continued

```
    50                  55                  60

Val Thr Asn Pro Val Asn Gly Gln Glu Ile Trp Tyr Tyr Glu Val Glu
65                  70                  75                  80

Ile Lys Pro Phe Thr His Gln Val Tyr Pro Asp Leu Gly Ser Ala Asp
                85                  90                  95

Leu Val Gly Tyr Asp Gly Met Ser Pro Gly Pro Thr Phe Gln Val Pro
            100                 105                 110

Arg Gly Val Glu Thr Val Val Arg Phe Ile Asn Asn Ala Glu Ala Pro
        115                 120                 125

Asn Ser Val His Leu His Gly Ser Phe Ser Arg Ala Ala Phe Asp Gly
    130                 135                 140

Trp Ala Glu Asp Ile Thr Glu Pro Gly Ser Phe Lys Asp Tyr Tyr Tyr
145                 150                 155                 160

Pro Asn Arg Gln Ser Ala Arg Thr Leu Trp Tyr His Asp His Ala Met
                165                 170                 175

His Ile Thr Ala Glu Asn Ala Tyr Arg Gly Gln Ala Gly Leu Tyr Met
            180                 185                 190

Leu Thr Asp Pro Ala Glu Asp Ala Leu Asn Leu Pro Ser Gly Tyr Gly
        195                 200                 205

Glu Phe Asp Ile Pro Met Ile Leu Thr Ser Lys Gln Tyr Thr Ala Asn
    210                 215                 220

Gly Asn Leu Val Thr Thr Asn Gly Glu Leu Asn Ser Phe Trp Gly Asp
225                 230                 235                 240

Val Ile His Val Asn Gly Gln Pro Trp Pro Phe Lys Asn Val Glu Pro
                245                 250                 255

Arg Lys Tyr Arg Phe Arg Phe Leu Asp Ala Ala Val Ser Arg Ser Phe
            260                 265                 270

Gly Leu Tyr Phe Ala Asp Thr Asp Ala Ile Asp Thr Arg Leu Pro Phe
        275                 280                 285

Lys Val Ile Ala Ser Asp Ser Gly Leu Leu Glu His Pro Ala Asp Thr
    290                 295                 300

Ser Leu Leu Tyr Ile Ser Met Ala Glu Arg Tyr Glu Val Val Phe Asp
305                 310                 315                 320

Phe Ser Asp Tyr Ala Gly Lys Thr Ile Glu Leu Arg Asn Leu Gly Gly
                325                 330                 335

Ser Ile Gly Gly Ile Gly Thr Asp Thr Asp Tyr Asp Asn Thr Asp Lys
            340                 345                 350

Val Met Arg Phe Val Val Ala Asp Asp Thr Thr Gln Pro Asp Thr Ser
        355                 360                 365

Val Val Pro Ala Asn Leu Arg Asp Val Pro Phe Pro Ser Pro Thr Thr
    370                 375                 380

Asn Thr Pro Arg Gln Phe Arg Phe Gly Arg Thr Gly Pro Thr Trp Thr
385                 390                 395                 400

Ile Asn Gly Val Ala Phe Ala Asp Val Gln Asn Arg Leu Leu Ala Asn
                405                 410                 415

Val Pro Val Gly Thr Val Glu Arg Trp Glu Leu Ile Asn Ala Gly Asn
            420                 425                 430

Gly Trp Thr His Pro Ile His Ile His Leu Val Asp Phe Lys Val Ile
        435                 440                 445

Ser Arg Thr Ser Gly Asn Asn Ala Arg Thr Val Met Pro Tyr Glu Ser
    450                 455                 460

Gly Leu Lys Asp Val Val Trp Leu Gly Arg Arg Glu Thr Val Val Val
465                 470                 475                 480
```

-continued

```
Glu Ala His Tyr Ala Pro Phe Pro Gly Val Tyr Met Phe His Cys His
                485                 490                 495

Asn Leu Ile His Glu Asp His Asp Met Met Ala Ala Phe Asn Ala Thr
            500                 505                 510

Val Leu Pro Asp Tyr Gly Tyr Asn Ala Thr Val Phe Val Asp Pro Met
        515                 520                 525

Glu Glu Leu Trp Gln Ala Arg Pro Tyr Glu Leu Gly Glu Phe Gln Ala
    530                 535                 540

Gln Ser Gly Gln Phe Ser Val Gln Ala Val Thr Glu Arg Ile Gln Thr
545                 550                 555                 560

Met Ala Glu Tyr Arg Pro Tyr Ala Ala Ala Asp Glu
                565                 570


<210> SEQ ID NO 5
<211> LENGTH: 21
<212> TYPE: PRT
<213> ORGANISM: Stachybotrys chartarum

<400> SEQUENCE: 5

Phe Val Asn Ser Gly Glu Asn Thr Ser Pro Asn Ser Val His Leu His
 1               5                  10                  15

Gly Ser Phe Ser Arg
            20


<210> SEQ ID NO 6
<211> LENGTH: 18
<212> TYPE: PRT
<213> ORGANISM: Stachybotrys chartarum

<400> SEQUENCE: 6

Gly Val Glu Pro Tyr Glu Ala Ala Gly Leu Lys Asp Val Val Trp Leu
 1               5                  10                  15

Ala Arg


<210> SEQ ID NO 7
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (12)...(12)
<223> OTHER INFORMATION: n = A,T,C or G

<400> SEQUENCE: 7

gtcaacagtg gngaraayac                                                  20


<210> SEQ ID NO 8
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (12)...(18)
<223> OTHER INFORMATION: n = A,T,C or G

<400> SEQUENCE: 8

gcggcctcat anggctcnac                                                  20
```